(12) United States Patent
Rosati et al.

(10) Patent No.: US 11,399,580 B2
(45) Date of Patent: Aug. 2, 2022

(54) DONNABLE BARRIER DEVICES, SYSTEMS, AND METHODS WITH TOUCHLESS CONTROL

(71) Applicants: THI Total Healthcare Innovation GmbH, Feistritz im Rosental (AT); Giorgio Rosati, San Cesareo (IT); Paul Gruber, Feistritz im Rosental (AT); Richard Nickl, Klagenfurt (AT); David Lee Cargille, East Windsor, NJ (US)

(72) Inventors: Giorgio Rosati, San Cesareo (IT); Paul Gruber, Feistritz im Rosental (AT); Richard Nickl, Klagenfurt (AT); David Lee Cargille, East Windsor, NJ (US)

(73) Assignee: THI TOTAL HEALTHCARE INNOVATION GMBH, Feistritz im Rosental (AT)

(*) Notice: Subject to any disclaimer, the term of this patent is extended or adjusted under 35 U.S.C. 154(b) by 931 days.

(21) Appl. No.: 16/067,932

(22) PCT Filed: Jan. 7, 2017

(86) PCT No.: PCT/US2017/012654
§ 371 (c)(1),
(2) Date: Jul. 3, 2018

(87) PCT Pub. No.: WO2017/120562
PCT Pub. Date: Jul. 13, 2017

(65) Prior Publication Data
US 2021/0228919 A1    Jul. 29, 2021

Related U.S. Application Data

(60) Provisional application No. 62/275,995, filed on Jan. 7, 2016.

(51) Int. Cl.
*A62B 18/00* (2006.01)
*A62B 18/04* (2006.01)
(Continued)

(52) U.S. Cl.
CPC .......... *A41D 13/1153* (2013.01); *A41D 1/002* (2013.01); *A41D 13/0025* (2013.01);
(Continued)

(58) Field of Classification Search
CPC ..... A62B 17/006; A62B 18/04; A62B 18/006; A62B 18/00; A62B 23/00; A62B 7/00;
(Continued)

(56) References Cited

U.S. PATENT DOCUMENTS

| 3,822,698 A * | 7/1974 | Guy | A62B 18/045 128/201.25 |
| 4,133,308 A * | 1/1979 | Lowe | A42B 3/288 128/201.25 |

(Continued)

FOREIGN PATENT DOCUMENTS

| CA | 2825277 A1 * | 8/2012 | ........... A42B 3/0406 |
| WO | WO-2011126887 A2 * | 10/2011 | ........ A61M 16/0627 |

(Continued)

OTHER PUBLICATIONS

International Search Report and Written Opinion for Corresponding international Application No. PCT/US2017/012654 (9 Pages) (dated Jun. 27, 2017).

*Primary Examiner* — Tu A Vo
(74) *Attorney, Agent, or Firm* — Lucas & Mercanti, LLP

(57) ABSTRACT

A barrier system, device, and method protects medical professionals and patients from exposure to contaminants and bodily fluids is provided. The system includes a head unit shaped to be worn over the head of the wearer; a hood positioned over the head unit; one or more sensors config-
(Continued)

ured to produce one or more sensor-output signals; and a controller connected to the one or more sensors and configured to produce one or more controller-output signals based on the one or more sensor-output signals. Further, a device inside a barrier system is controlled by (a) sensing one or more characteristics; (b) producing one or more sensor signals based on the sensed one or more characteristics; (c) converting and/or processing the one or more sensor signals to produce one or more controller-output signals; and (d) controlling the device based on the one or more controller-output signals.

19 Claims, 22 Drawing Sheets

(51) Int. Cl.
    A62B 9/00        (2006.01)
    A62B 17/04      (2006.01)
    A62B 18/08      (2006.01)
    A62B 7/00        (2006.01)
    A41D 13/11      (2006.01)
    A42B 3/04       (2006.01)
    A42B 3/00       (2006.01)
    A61M 16/00      (2006.01)
    A42B 3/28       (2006.01)
    A61M 16/16      (2006.01)
    A41D 1/00       (2018.01)
    A41D 13/002     (2006.01)

(52) U.S. Cl.
    CPC ...... *A41D 13/1161* (2013.01); *A41D 13/1184* (2013.01); *A42B 3/046* (2013.01); *A42B 3/286* (2013.01); *A61M 16/0003* (2014.02); *A61M 16/0066* (2013.01); *A61M 16/161* (2014.02); *A62B 7/00* (2013.01); *A62B 9/006* (2013.01); *A62B 17/04* (2013.01); *A62B 18/003* (2013.01); *A62B 18/045* (2013.01); *A62B 18/08* (2013.01); *A61M 2205/3368* (2013.01); *A61M 2205/50* (2013.01); *A61M 2205/80* (2013.01); *A61M 2230/432* (2013.01); *A61M 2230/63* (2013.01)

(58) Field of Classification Search
    CPC ........... A62B 7/10; A62B 17/00; A62B 17/04; A62B 18/003; A62B 23/02; A62B 18/045; A62B 18/08; A41D 13/0025; A41D 13/1153; A42B 3/046; A42B 3/286
    See application file for complete search history.

(56) References Cited

U.S. PATENT DOCUMENTS

| | | | | |
|---|---|---|---|---|
| 4,430,995 A * | 2/1984 | Hilton | ............... | A61M 16/0069 128/204.21 |
| 4,502,480 A * | 3/1985 | Yamamoto | ........... | A62B 18/045 128/201.15 |
| 4,590,951 A * | 5/1986 | O'Connor | ............ | A62B 18/006 128/204.23 |
| 5,054,480 A * | 10/1991 | Bare | .................... | A62B 18/045 128/201.25 |
| 5,104,430 A * | 4/1992 | Her-Mou | ............. | A62B 18/006 128/205.29 |
| 5,113,853 A * | 5/1992 | Dickey | ................ | A62B 18/045 128/200.28 |
| 5,283,914 A * | 2/1994 | James | ..................... | A42B 3/16 128/201.24 |
| 5,533,500 A * | 7/1996 | Her-Mou | ............... | A42B 3/288 128/201.24 |
| 5,592,936 A * | 1/1997 | Thomas, Jr. | ........... | A41D 13/11 128/201.24 |
| 5,711,033 A * | 1/1998 | Green | .................... | A42B 3/286 2/171.3 |
| 5,887,281 A * | 3/1999 | Green | .................... | A42B 3/286 2/424 |
| 6,792,944 B1 * | 9/2004 | Green | ................... | A42B 3/286 128/201.22 |
| 2001/0032348 A1 * | 10/2001 | Diaz | .................. | A41D 13/1153 2/171.3 |
| 2005/0011516 A1 * | 1/2005 | Lukas | .................. | A62B 18/006 128/201.22 |
| 2005/0060788 A1 * | 3/2005 | Green | ................ | A41D 13/1153 2/171.3 |
| 2005/0109337 A1 | 5/2005 | Diaz | | |
| 2006/0048776 A1 * | 3/2006 | Cunningham | ......... | A62B 17/04 128/201.22 |
| 2006/0213523 A1 * | 9/2006 | VanDerWoude | ....... | A42B 3/286 128/863 |
| 2007/0028372 A1 * | 2/2007 | VanDerWoude | ....... | A42B 3/286 2/457 |
| 2007/0044800 A1 * | 3/2007 | Church | ................. | F04D 27/004 128/205.29 |
| 2007/0151002 A1 | 7/2007 | Klotz | | |
| 2007/0240719 A1 * | 10/2007 | Duarte | ................... | A62B 29/00 128/205.27 |
| 2007/0277294 A1 * | 12/2007 | Green | .................. | A62B 18/045 2/410 |
| 2009/0151054 A1 * | 6/2009 | VanDerWoude | ... | A41D 13/1153 2/410 |
| 2010/0037891 A1 * | 2/2010 | Walker | .................... | A62B 17/04 128/201.23 |
| 2010/0081411 A1 * | 4/2010 | Montenero | ........ | G08B 21/0233 455/404.2 |
| 2010/0083967 A1 * | 4/2010 | Kuriyama | ................ | A62B 7/10 128/204.23 |
| 2010/0108067 A1 * | 5/2010 | Walker | ................. | A62B 18/084 128/205.24 |
| 2010/0224194 A1 * | 9/2010 | Walker | .................. | A62B 18/02 128/205.24 |
| 2010/0263671 A1 * | 10/2010 | Walker | .................. | A62B 17/04 128/205.25 |
| 2010/0294270 A1 * | 11/2010 | Curran | ................. | A62B 18/045 128/201.23 |
| 2010/0313892 A1 * | 12/2010 | Shigematsu | ........... | A62B 18/10 128/207.12 |
| 2011/0215931 A1 * | 9/2011 | Callsen | .................. | A42B 3/046 340/573.1 |
| 2011/0240026 A1 * | 10/2011 | Ausen | ..................... | A42B 3/286 128/205.12 |
| 2011/0265790 A1 * | 11/2011 | Walker | .................. | A62B 17/04 128/201.23 |
| 2012/0138051 A1 * | 6/2012 | Curran | .................. | A62B 18/006 128/201.25 |
| 2012/0246809 A1 * | 10/2012 | Elam | ..................... | A42B 3/286 2/424 |
| 2013/0014752 A1 * | 1/2013 | Ausen | .................... | A62B 18/045 128/201.25 |
| 2013/0091624 A1 * | 4/2013 | Czajka | ................. | A41D 13/1218 2/456 |
| 2013/0092164 A1 * | 4/2013 | Curran | .................. | A62B 9/006 128/204.21 |
| 2013/0139818 A1 * | 6/2013 | Billingsley | ............. | A42B 3/286 128/205.12 |
| 2013/0142656 A1 * | 6/2013 | Hamilton | ............... | F04D 27/004 416/204 R |
| 2013/0152919 A1 * | 6/2013 | Billingsley | ............. | A62B 7/10 128/201.25 |
| 2013/0152920 A1 * | 6/2013 | Billingsley | ............. | A62B 7/10 128/201.25 |
| 2013/0186279 A1 * | 7/2013 | Dwyer | ............... | G01N 21/3151 96/418 |
| 2013/0327325 A1 * | 12/2013 | VanDerWoude | ... | A41D 13/0025 128/201.29 |
| 2015/0000651 A1 * | 1/2015 | Palacharla | ............ | A62B 9/006 128/202.22 |

(56) References Cited

U.S. PATENT DOCUMENTS

| | | | | |
|---|---|---|---|---|
| 2015/0114389 A1* | 4/2015 | Sernfalt | ............... | A62B 18/006 |
| | | | | 128/202.22 |
| 2015/0211534 A1* | 7/2015 | Volmer | ............... | F04D 25/0673 |
| | | | | 417/45 |
| 2015/0375018 A1* | 12/2015 | Franke | ................ | A62B 18/082 |
| | | | | 2/417 |
| 2016/0353827 A1* | 12/2016 | Verela | .................... | A42B 3/283 |

FOREIGN PATENT DOCUMENTS

| | | | | |
|---|---|---|---|---|
| WO | WO-2012111030 A1 * | 8/2012 | ......... | A41D 13/0025 |
| WO | WO-2014160149 A2 * | 10/2014 | ............. | A42B 3/286 |

* cited by examiner

Step 1

Step 2

DONNABLE BARRIER DEVICES, SYSTEMS, AND METHODS WITH TOUCHLESS CONTROL

CROSS-REFERENCE TO RELATED APPLICATIONS

This application is a 371 of PCT/US2017/012654, filed Jan. 7, 2017, which claims the benefit of U.S. Provisional Patent Application No. 62/275,995, filed Jan. 7, 2016.

FIELD OF THE INVENTION

Embodiments of the invention relate generally to barrier devices, filtration devices, and personal protection systems for use in hazardous environments, including medical, surgical, and field environments. Certain embodiments protect medical professionals from exposure to airborne contaminants and bodily fluids and also protect patients, medical professionals, and observers from cross-contamination during surgical procedures. Certain embodiments relate more particularly to helmets, hoods, masks, face shields, togas, or other wearable apparatuses for protecting a healthcare professional, patient, or observer from exposure to biohazardous materials during surgery, other medical procedures, emergency medicine, treatment of victims in the field, and the like.

BACKGROUND OF THE INVENTION

Barrier devices and personal protection systems are used in medical and surgical procedures to provide a sterile barrier between the surgical personnel and the patient. During such procedures (and especially during orthopedic operations), a drill or powered saw often generates spray, splash, and aerosol from a patient's surgical wound to the surgeon. This exposes the surgeon to a risk of infection. Traditional surgical masks and cups are not capable of completely keeping the sterility of the surgical wound. In some cases, bodily materials from a surgical team (e.g., sweat, hair, dandruff, or even saliva) may infect the patient. For these reasons, especially in orthopedic surgery, a surgical helmet has been used for many years. A conventional surgical helmet may include a battery-powered fan for air circulation and a sterile hood that covers the helmet and has a transparent visor, lens, or other vision element.

One such system is disclosed in U.S. Pat. No. 5,054,480, the contents of which are incorporated herein by reference discloses that basic structure of such a system. Specifically, the traditional system includes a helmet that supports a toga, also known as a drape or hood. (The terms "toga", "drape", and "hood" are used interchangeably herein and are intended to have the same meaning.) This assemblage is worn by medical personnel who want to establish the sterile barrier. The hood includes a transparent face shield. The helmet includes a ventilation unit that includes a fan. The ventilation unit draws air through the hood so the air is circulated around the wearer. This reduces both the amount of heat that is trapped within the toga/hood and the carbon dioxide ($CO_2$) that builds up in this space. It is further known to mount a light to the helmet. The light, which is directed through face shield illuminates the surgical site.

Donning a hood creates a closed chamber around the operator's head, which represents both a heating element (by means of radiation and/or convection) and a source of hot and humid respiratory air with significant $CO_2$ concentrations up to 40,000 ppm. Without air exchange between the chamber and the ambient environment, a so called "sauna effect" is created, leading to temperatures of up to 32° C., humidity levels of up to 85% (relative humidity) and $CO_2$ concentrations of up to 40,000 ppm inside the chamber. To avoid this effect, state of the art surgical protection systems include hoods with a filter element, which supports air exchange and provides breathability as well. This is typically accomplished using fans that move air into the chamber and circulate air within the chamber.

Other personal protection systems are disclosed in U.S. Pat. No. 6,481,019 to Diaz et al., in U.S. Pat. No. 9,173,437 to VanDerWoude et al., and in U.S. patent application Ser. No. 13/984,908 filed by Giorgio Rosati et al., the contents of each of which is incorporated by reference in its entirety. VanDerWoude et al., for example, describes a system having a hood, a fan, a light, and a helmet with control switches that a user actuates by hand.

Problems to be Solved

The present inventors have recognized and identified a number of drawbacks of conventional filtration apparel systems for health care professionals.

Some systems establish a bypass between the operator's head chamber and the intake air funnel of the main fan, which allows waste air from inside the operator's head chamber to be drawn back into the chamber, thereby reducing the fresh air exchange rate, especially with filters having low breathability (i.e., high bacterial filtration efficiency). A significant portion of air delivered by the main intake fan is therefore waste air instead of fresh ambient air. This effect increases with decreasing breathability of filter materials.

Another drawback relates to difficulty in donning. After putting on the helmet, adjusting it, and connecting the power line of the helmet to the battery pack, a user of a conventional hood dons the device in three steps, by: (1) unfolding the hood, (2) attaching the vision element to the helmet, and (3) pulling the fabric over the helmet.

Known donning concepts require assistance by at minimum one sterile or non-sterile supporting individual in the operating theatre to avoid breaching sterility (of all outer surfaces of the gown) during donning. Conventional hoods use fixed-position vision element frames on the helmet. During attachment of the hood or toga to the front of the face, visibility is greatly reduced because of the opaque nature of the fabric. This prohibits the user from performing the next step—pulling the fabric over the helmet—by himself or herself, since the likelihood of contacting the outside of the fabric with a non-sterile body part is too high. Therefore, a sterile-dressed supporting individual is required to perform fabric-pulling step (3). Alternatively, a non-sterile dressed supporting individual might also perform step (3), with the limitation to touch only the inside of the fabric or only portions of the fabric that are subsequently covered by sterile surgical gowns.

Another drawback relates to difficulty in fan-speed control. Required air exchange rates depend, among other factors, on ambient air temperature and humidity, physical activity during a surgical procedure, specific heat output of the human body, and mental stress level, as well as personal preferences for air conditions and air quality. Some conventional surgical protection systems offer user-adjustability of fan speeds to increase or reduce the air input. A higher or lower air input causes a higher or lower air circulation that may improve the comfort of the surgeon. The quantity of air circulation needed may vary according to personal preferences of the surgeon or his or her physical activity during the different phases of an operation, which may be lighter or heavier at various moments.

Conventional surgical helmets regulate the fan speed by a button or switch placed somewhere on the helmet. To adjust fan speed, a surgeon must press a mechanical button or activate a touch switch located below the sterile barrier (hood or toga) and therefore must touch the barrier. This is neither safe nor convenient. During operation, the helmet is often covered by a sterile drape, and the surgeon must wear surgical gloves. Activating the switch is often difficult and inconvenient, because the surgeon can neither see nor easily feel where the switch is. It is unsafe, because the button or switch might become contaminated in certain circumstances, e.g., by unnoticed contact with a lamp, a colleague, or an unsterile part. By touching the switch, which is no longer sterile, the surgeon may contaminate his hands, other people, and other surfaces.

SUMMARY OF THE INVENTION

Embodiments of the disclosure solve these problems and provide other benefits through a personal protection system and device employing one or more of the following features: an intake air duct with enhanced fresh air circulation; an easy-donning hood-helmet interface; a free-flow main air duct; automatic airflow control; and a touchless user interface.

In one embodiment, the invention is a barrier system. The system comprises a head unit (e.g., 708) shaped to be worn over the head of the wearer; a hood (e.g., 704) positioned over the head unit and forming a chamber (e.g., 212); one or more sensors (e.g., 1902) located within the chamber and configured to produce one or more sensor-output signals; and a controller (e.g., 1904) connected to the one or more sensors and configured to produce one or more controller-output signals based on the one or more sensor-output signals.

In another embodiment, the invention is a method of controlling a device inside a barrier system comprising a head unit (e.g., 708), a hood (e.g., 704), one or more sensors (e.g., 1902), and a controller (e.g., 1904). The method comprises: (a) sensing one or more characteristics; (b) producing one or more sensor signals based on the sensed one or more characteristics; (c) converting and/or processing the one or more sensor signals to produce one or more controller-output signals; and (d) controlling the device based on the one or more controller-output signals.

In another embodiment, the invention is a barrier device. The barrier device comprises: a head unit (e.g., 708) shaped to be worn over the head of the wearer; a hood (e.g., 704) positioned over the head unit and forming a chamber (e.g., 212); one or more sensors (e.g., 1902) located within the chamber and configured to produce one or more sensor-output signals; and a controller (e.g., 1904) connected to the one or more sensors and configured to produce one or more controller-output signals based on the one or more sensor-output signals.

In another embodiment, the invention is an apparatus for controlling a device inside a barrier system comprising a head unit (e.g., 708), a hood (e.g., 704), one or more sensors (e.g., 1902), and a controller (e.g., 1904). The apparatus comprises: (a) means for sensing one or more characteristics; (b) means for producing one or more sensor signals based on the sensed one or more characteristics; (c) means for converting and/or processing the one or more sensor signals to produce one or more controller-output signals; and (d) means for controlling the device based on the one or more controller-output signals

BRIEF DESCRIPTION OF THE DRAWINGS

Other advantages of the present invention will be readily appreciated and better understood by reference to the following detailed description, when considered in connection with the accompanying drawings wherein.

DETAILED DESCRIPTION OF THE INVENTION

Embodiments of the disclosure solve these problems and provide other benefits by employing one or more of the following features: an intake air duct with enhanced fresh air circulation; an easy-donning hood-helmet interface; a free-flow main air duct; automatic airflow control; and a touchless user interface.

Figure 1:
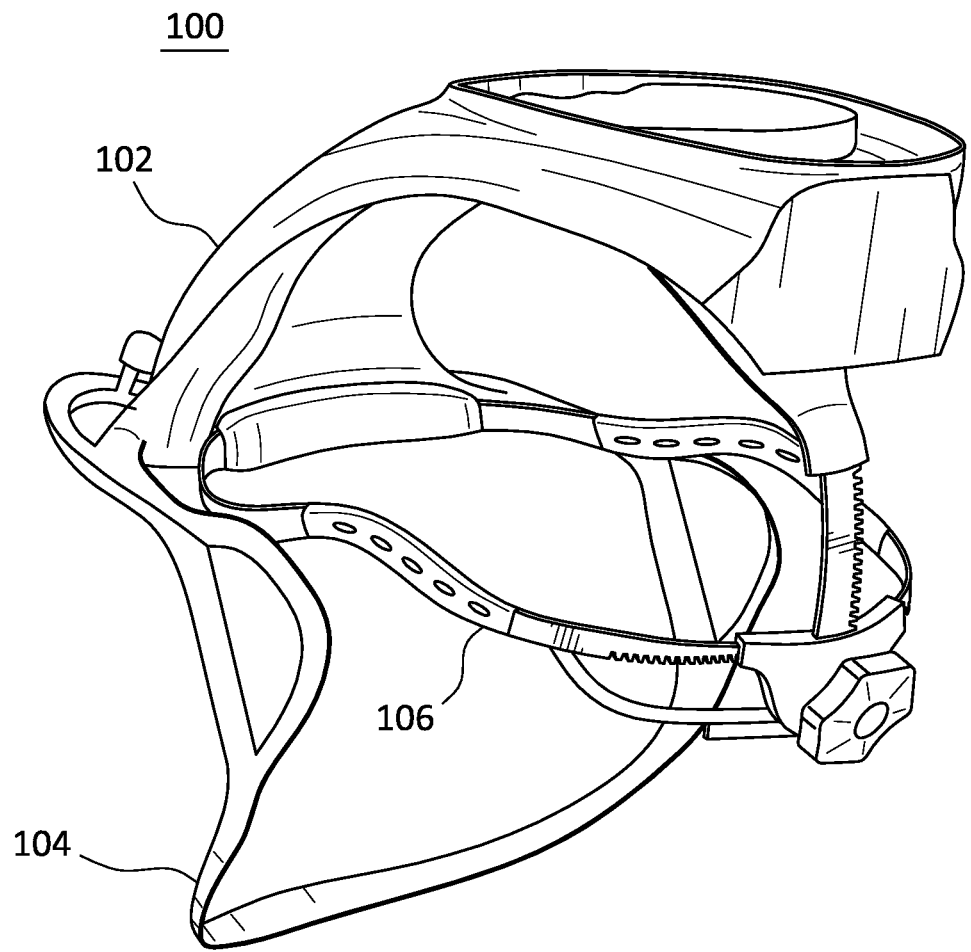
FIG. 1 is a perspective view of an exemplary surgical helmet in an embodiment of the disclosure.

With reference to FIG. 1, an exemplary surgical helmet 100 in an embodiment of the invention comprises: a head unit 102, a lensframe 104 mounted on the head unit 102, and an adjustable head strap 106 for securing head unit 102 on a user's head.

Figure 2:
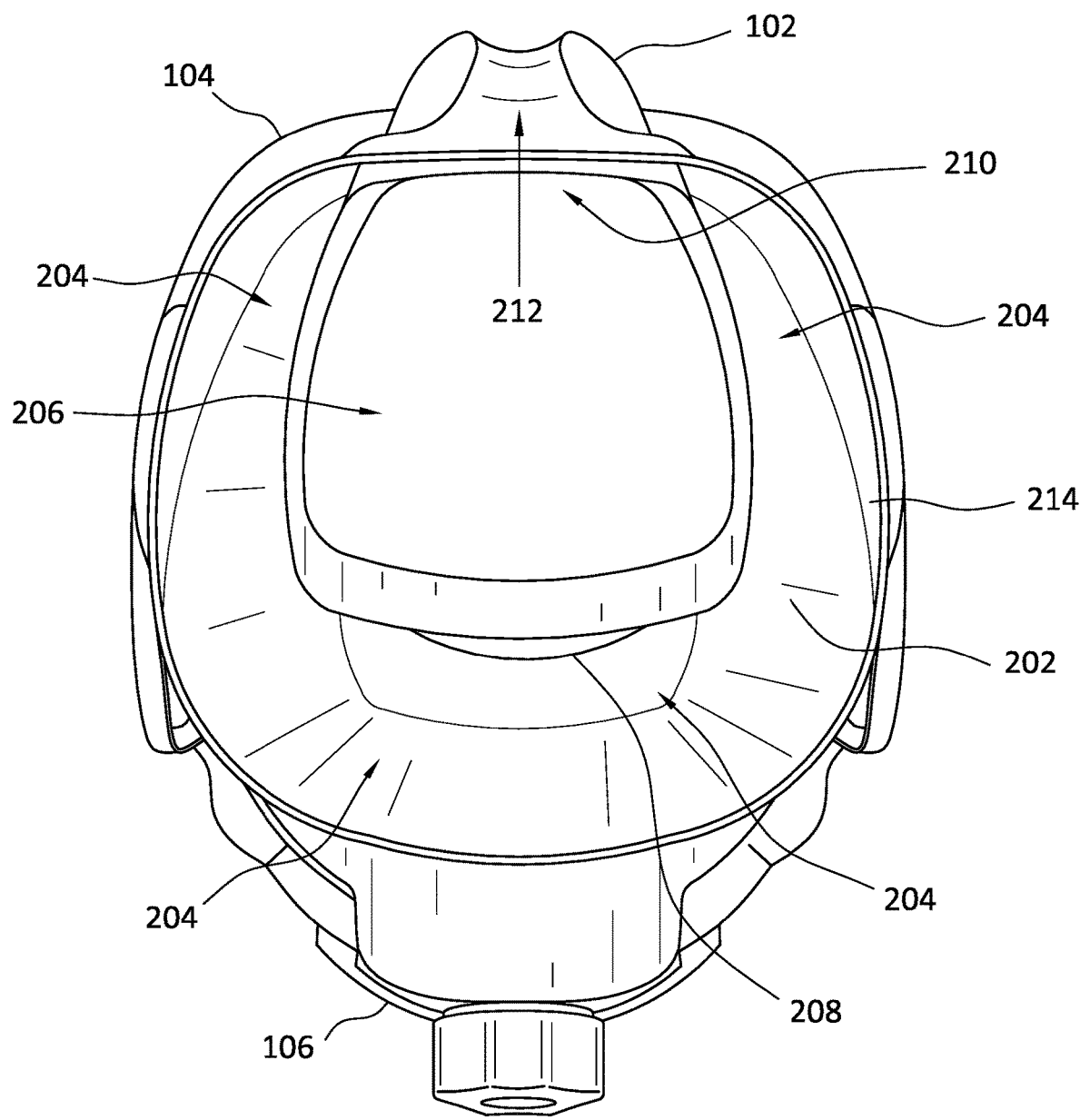
FIG. 2 is a top view of the surgical helmet shown in FIG. 1.

With reference to FIG. 2, the head unit 102 comprises a fan intake duct 202 (forming zone 1) configured to guide intake airflow 204, a mounting plate 206, an intake fan 208 mounted on the underside of mounting plate 206, a fan outlet 210 directed into a main air duct 212 located within a portion of head unit 102, and a sealing edge 214.

Intake Air Duct with Enhanced Fresh Air Circulation

Figure 3:
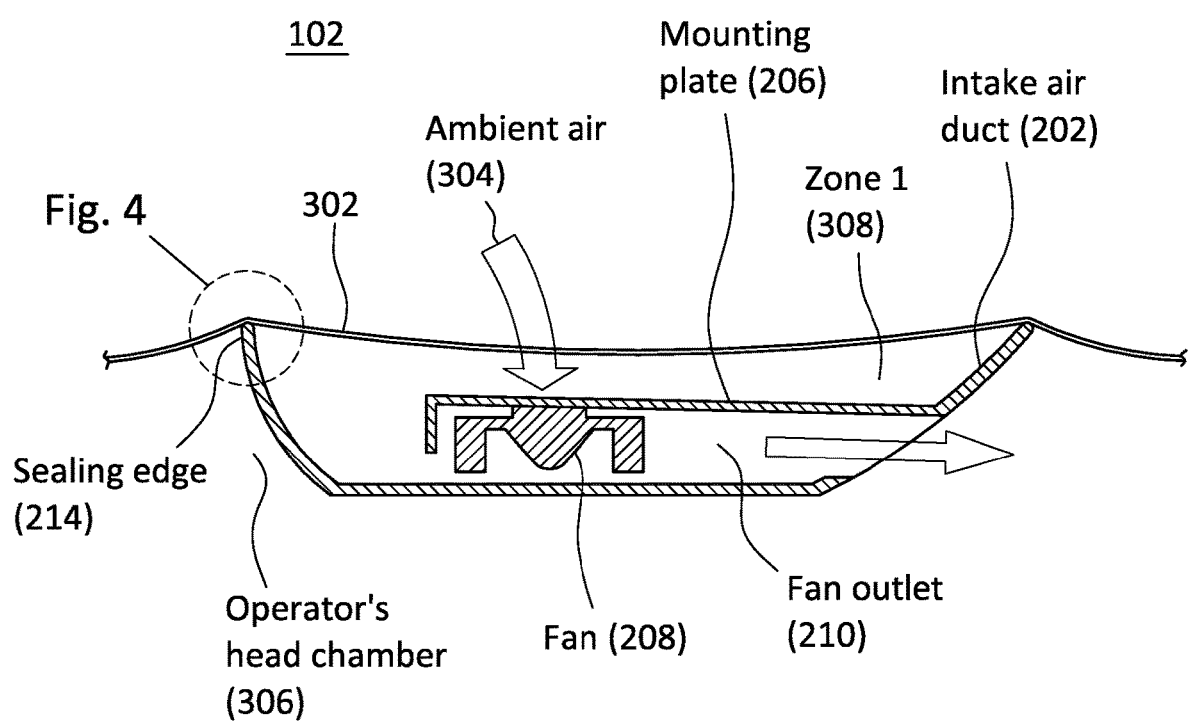
FIG. 3 is a cross-sectional view of a first exemplary head unit having a top-mounted fan in an embodiment of the disclosure.

Embodiments of the disclosure may include an intake air duct that is adapted to provide enhanced fresh air circulation. FIGS. 2 and 3 show an exemplary intake air duct 202 in one embodiment of the disclosure.

With reference to FIG. 2, head unit 102 comprises the intake air duct 202 in combination with intake fan 208 and a filter material 302 (e.g., formed by the fabric of a hood) that creates a plenum 308 (Zone 1), which is shown in FIG. 3. During operation, fresh ambient air 304 is sucked by the fan 208 through the filter 302 into the plenum 308 (zone 1) and further through the fan 208 into the operator's head chamber 306. The fan intake duct 202 is sealed off against the filter material 302 and the fan 208, creating a local area of low pressure, thereby forcing the air to be drawn in only through the filter material 302. This arrangement ensures that no bypass between the operator's head chamber 306 and the fan intake duct 202 is created.

The sealing between the fan intake duct 202 and the filter material 302 is promoted by hydrodynamic forces because of local low pressure in the intake air duct 202 (zone 1). This effect helps to create a seal, even in the event that the filter material 302 is placed loosely on the fan intake duct 202, without additional fixation means, as shown in FIG. 3. The sealing edge 214 seals reliably, because it is dimensioned such that the filter is concave (angle x°>0 relative to the general plane of the sealing edge 214) because of negative pressure.

The sealing edge 214 further seals reliably through protrusion of the filter material 302 over the surrounding surfaces. Additionally, a reliable seal between the fan 208 and the fan intake duct 202 is provided.

Figure 4:
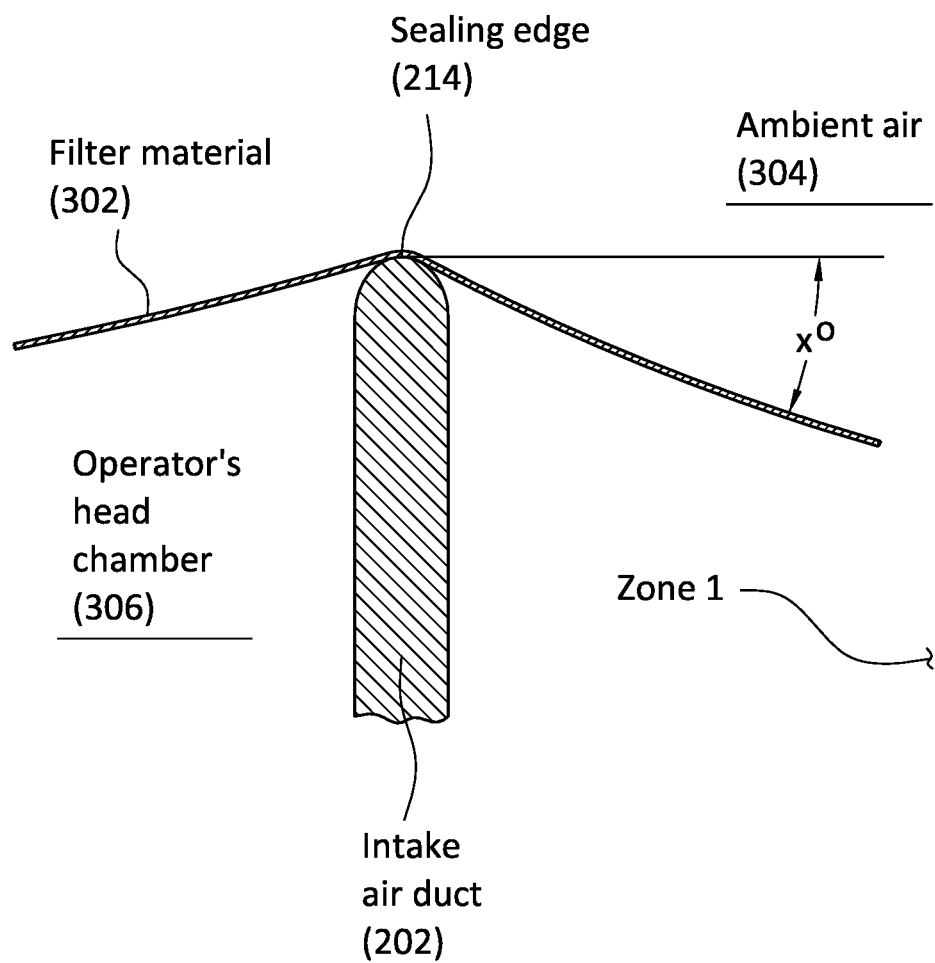
FIG. 4 is a cross-sectional, scaled view of a portion of the head unit shown in FIG. 3.
Figure 5:
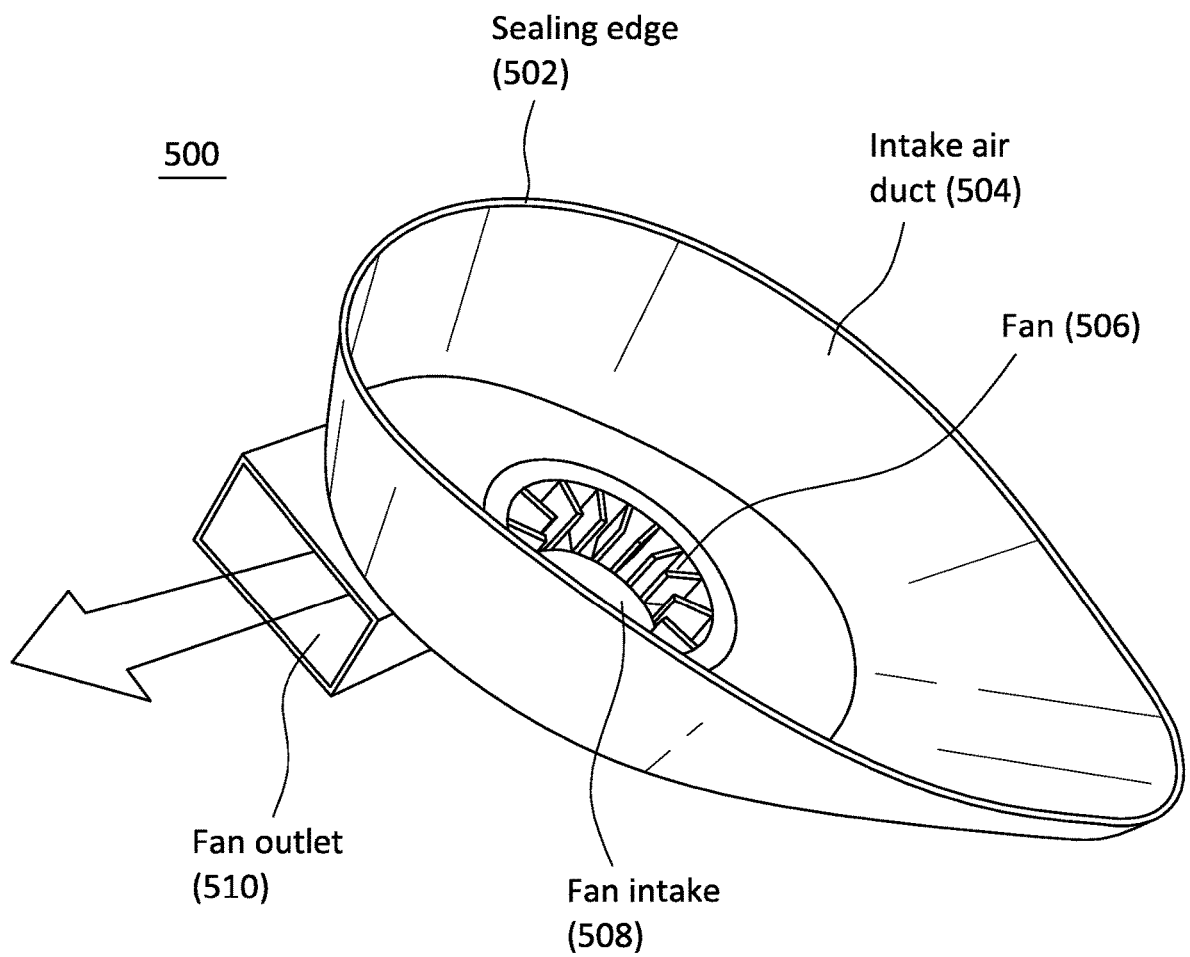
FIGS. 5 and 6 show a second exemplary head unit having a bottom-mounted fan in an embodiment of the disclosure.
Figure 6:
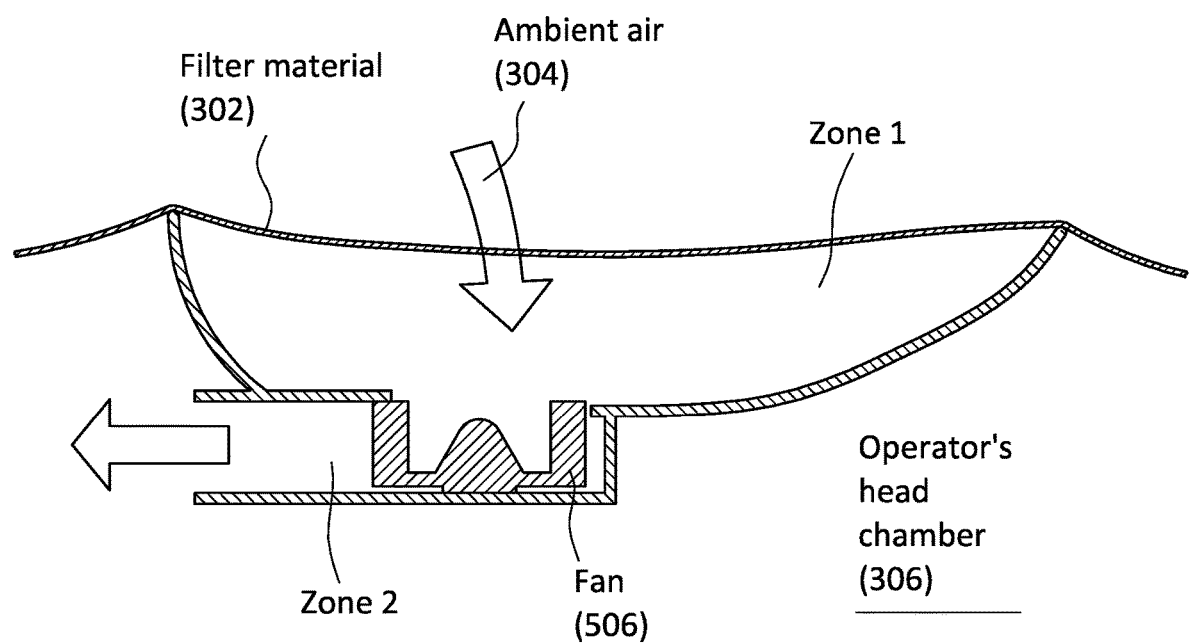

FIGS. 5 and 6 show another exemplary intake air duct 504 in another embodiment of the disclosure. Like the embodiment shown in FIG. 3, a fan assembly 500 comprises an intake air duct 504 having a sealing edge 502, and a fan 506 having a fan intake 508 and a fan outlet 510. Fan assembly 500, however, is configured so that the fan is recessed below the upper surface of intake air duct 506, and it is bottom-mounted within the fan outlet 510, rather than top-mounted on elevated mounting plate 206. In contrast, the embodiment shown in FIG. 4 does not need an elevated mounting plate.

The present inventors have determined through experimentation that, in one embodiment, the negative pressure created by fan 208 is within a predetermined negative-pressure range having a lower-boundary vacuum pressure and an upper-boundary vacuum pressure. The lower-boundary vacuum pressure is the pressure at which the filter material 302 is pulled down so far that it interferes with the intake airflow 202. At the lower-boundary vacuum pressure, the filter material reduces the intake airflow so much that the airflow is insufficient for adequate ventilation, which renders the helmet unusable. The upper-boundary vacuum pressure is the pressure at which the filter material 302 fails to provide an adequate seal at sealing edge 214. The upper- and lower-boundary vacuum pressures depend upon the characteristics of the filter material 302.

The present inventors further determined through experimentation that the intake airflow is a nonlinear function having an inflection point at an optimal vacuum pressure that varies depending on the type of filter material. Assuming that a fan starts operation at an initial ambient pressure, the magnitude of the negative pressure initially increases as the fan speed increases. As the negative pressure increases, the intake airflow correspondingly increases as a positive function of the negative pressure, and eventually reaches a maximum amount of airflow at the optimal vacuum pressure.

Surprisingly, the present inventors discovered that if the negative pressure continues to increase past the optimal pressure, then the airflow begins to decrease, rather than to increase as one would ordinarily expect. When the magnitude of the negative pressure is larger than the optimal vacuum pressure, the intake airflow is therefore a negative function of the negative pressure. These results were counterintuitive and unexpected.

The inventors also found that, even for a given fan, the way in which the fan is mounted and the shape of the intake air duct 202 may result in more airflow or less airflow, depending on the magnitude of the negative pressure exerted upon the filter material 302 and on the optimal vacuum pressure for a given filter material. They further found that, when certain fans are top-mounted within head unit 102 as shown in FIG. 3, they exert a smaller vacuum pressure, whereas when those fans are bottom-mounted (as shown in FIG. 4, described below), they exert a greater vacuum pressure. The inventors further discovered that, in certain circumstances, the vacuum pressure created by such fans may exceed the optimal vacuum pressure (i.e., a pressure that is past the inflection point), such that reducing the vacuum pressure by top-mounting the fan yields a greater airflow, rather than a smaller airflow.

The inventors accordingly have discovered and identified a problem in which certain bottom-mounted fans yielded inadequate ventilation, and solved the problem by providing the elevated mounting plate shown in FIG. 3, which allows a fan to be top-mounted, and thereby reduces the vacuum pressure and increases the airflow. Further, when such fans are top-mounted instead of bottom-mounted, the fan size may be reduced because of the greater airflow, thereby achieving an unexpected increase in efficiency and a cost savings that makes the helmet more competitive in the marketplace.

Easy-Donning Hood-Helmet Interface

Embodiments of the disclosure may include an easy-donning hood-helmet interface. FIGS. 7-16 show an exemplary easy-donning hood-helmet interface, in one embodiment of the disclosure. In this embodiment, a vision element frame 706 (hereinafter referred to as lensframe 706) is adapted to swivel around pivot points or along a slotted link on head unit 708, thereby allowing the user full visibility during donning, which reduces the likelihood of unintentional contact with the gown. Color-coded ribbons 702 (colored grey (702b) and white (702a), in this example) allow the user to pull the hood 704 over his or her own head, maintaining a safe distance to the outer surface of the hood 704 itself.

Figure 7:
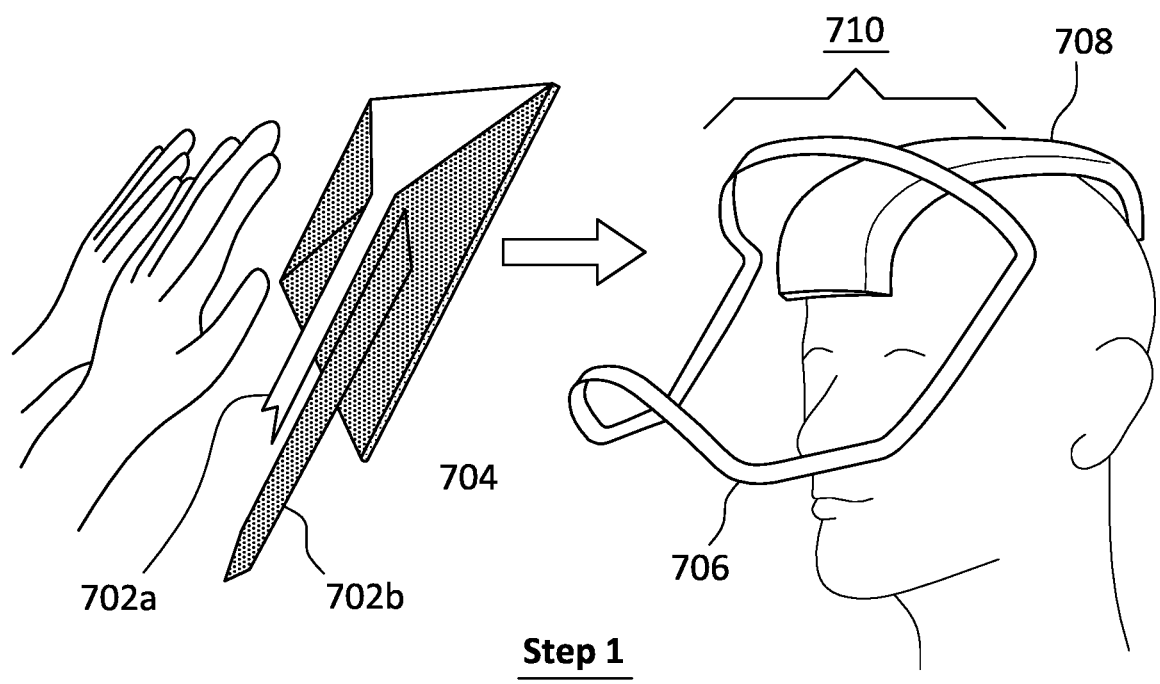
FIGS. 7-15 show an exemplary easy-donning hood-helmet interface in an embodiment of the disclosure.

The following steps are performed in an exemplary donning sequence consistent with one embodiment of the disclosure:

As FIG. 7 shows, Step 1 involves unpacking and unfolding the outer protection garment of the hood 704. The hood 704 is folded inside-out to reduce risk of contamination. Color-coded ribbons 702a, 702b indicate where to grab the hood 704 to complete donning. These ribbons will rest underneath the surgical gown after donning.

Figure 8:
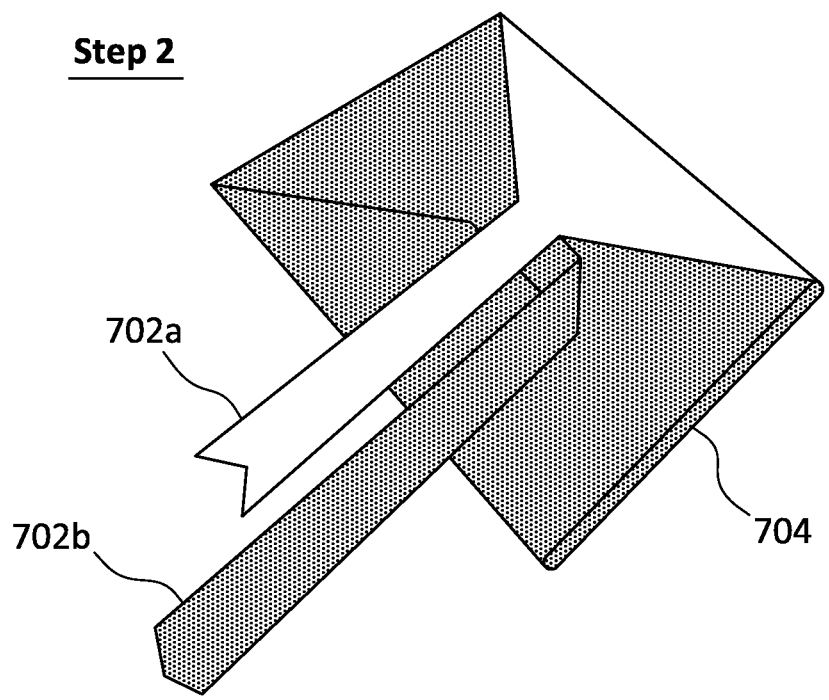

Turning now to FIG. 8, Step 2 involves attaching the folded hood 704 on the lensframe 706, in an open position. Geometrical guidance is provided by a centering hook (shown in FIG. 16), located at the lower center of the lensframe 706 (where it is easily visible the lensframe is folded into an open position) as well as several hook-and-loop fasteners or magnets along the lensframe 706.

Figure 9:
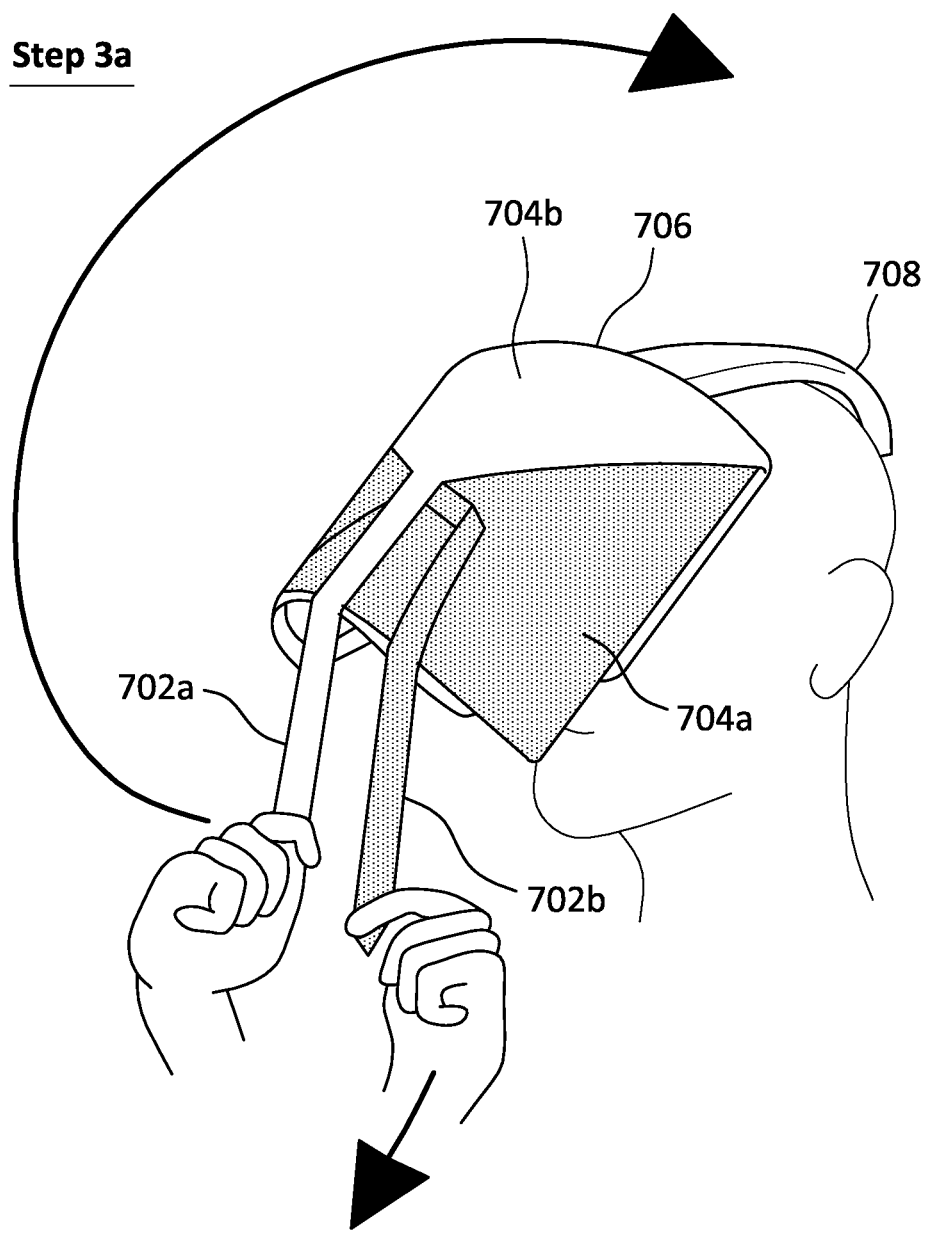
Figure 10:
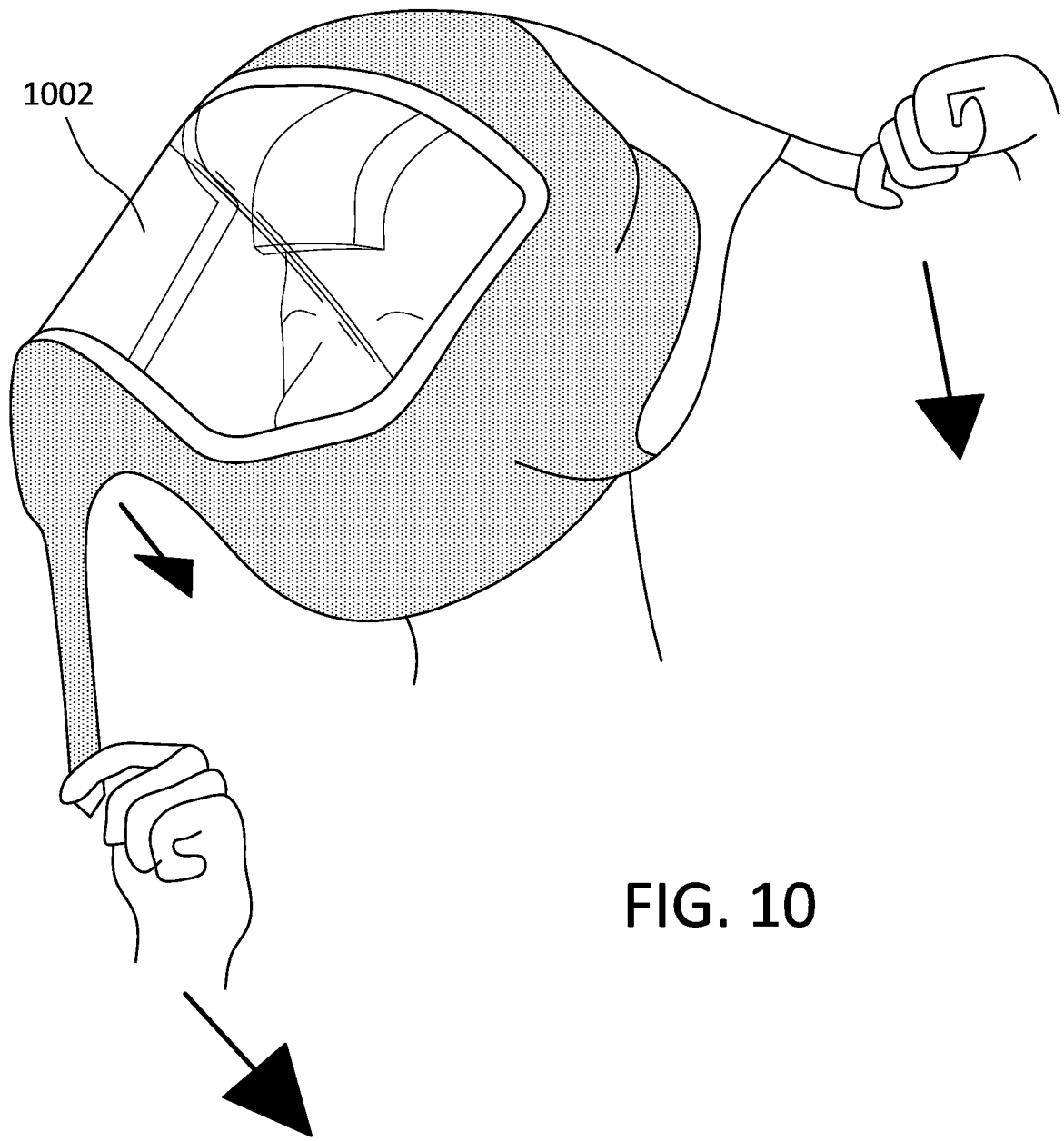
Figure 11:
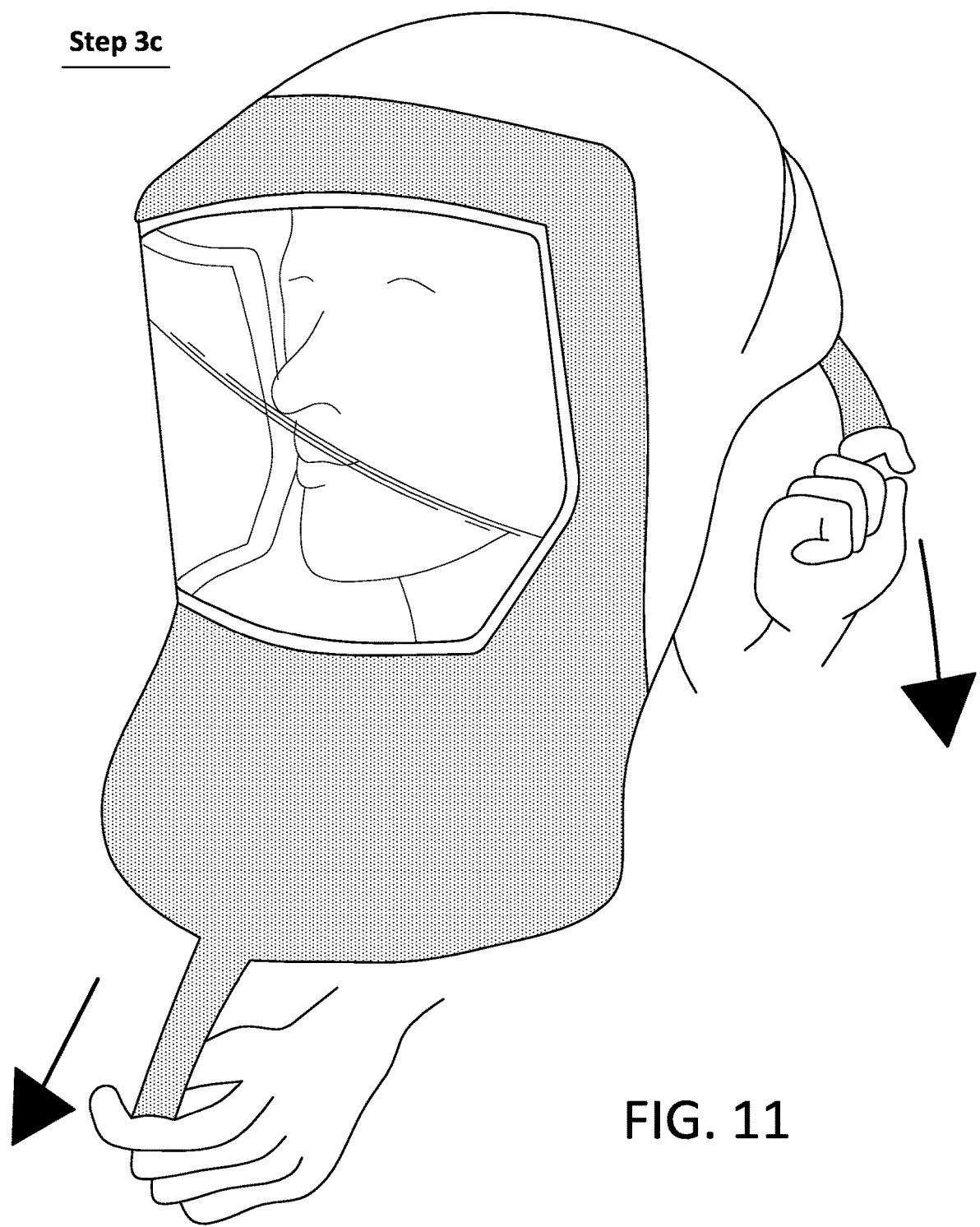

FIGS. 9 through 11 show the substeps 3a, 3b, and 3c of Step 3, which involves pulling the hood front 704a (shown shaded in grey) and back 704b (shown colored white) over the helmet 710 (formed by lensframe 706 and head unit 708) and the user's head, using the color-coded ribbons 702. The ribbons are easily visible because of the lensframe 706 being folded into the open position. The lengths of the ribbons 702 are selected so as to avoid unintentional contact with the outer surface of the hood 704. In the process of pulling the front 704a (grey) towards the user's chest and the back 704b up and over the user's head, the lensframe will fold automatically into operational position, where a transparent window portion 1002 (hereinafter referred to as lens 1002) of the hood front 704a is positioned over lensframe 706.

Figure 12:
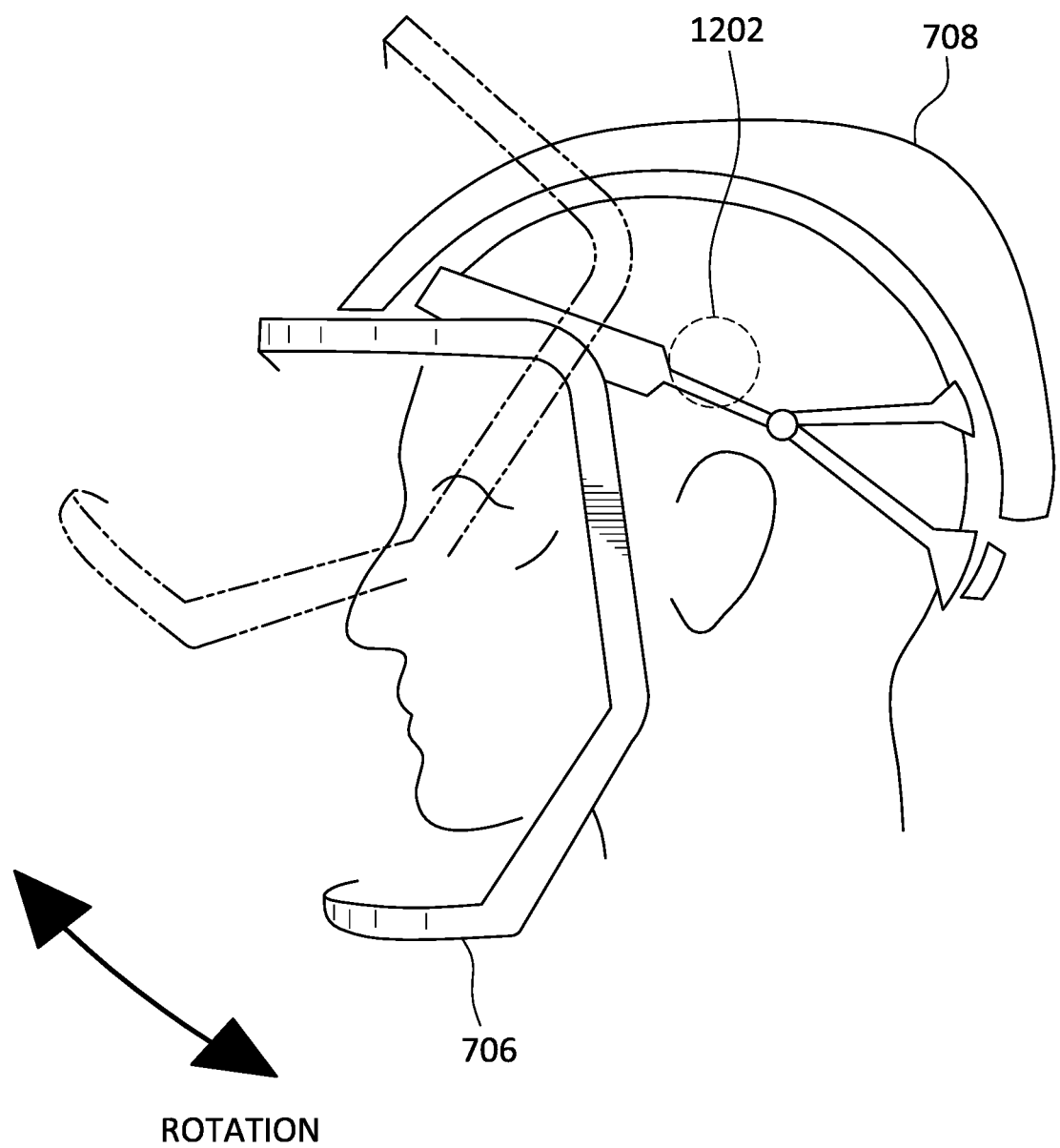
Figure 13:
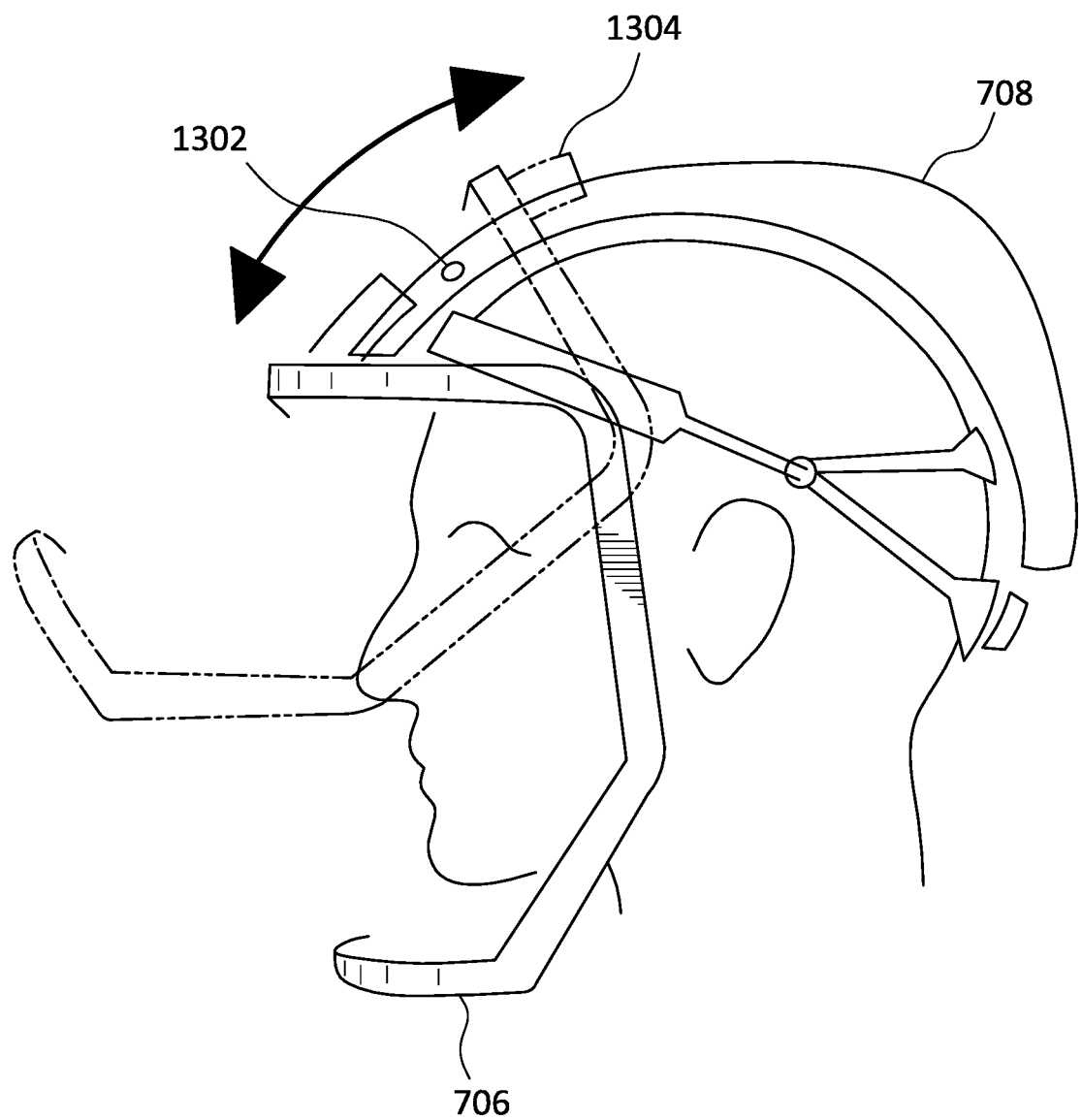

FIG. 12 shows an exemplary pivot-point-type swivel mechanism, and FIG. 13 shows an exemplary slotted-link-type swivel mechanism. One or both of these mechanisms may be employed in embodiments of the disclosure. The swiveling action of the lensframe 706 is a rotation around pivot points 1202 (shown in broken lines in FIG. 12) or a sliding motion along a slotted link formed by slot 1302 (shown in broken lines in FIG. 13) in head unit 708 and tab 1304 of lensframe 706.

Figure 14:
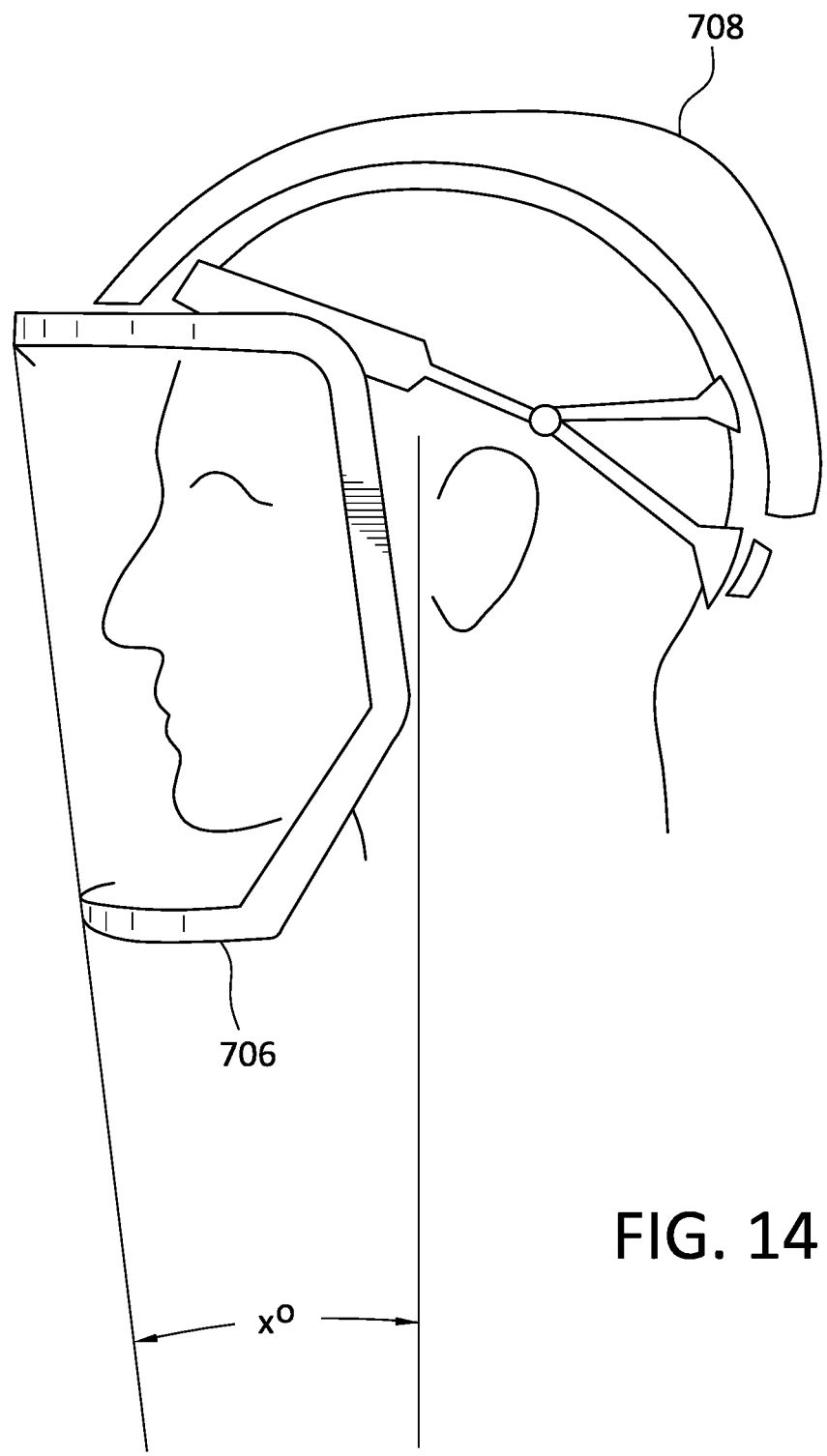

With reference now to FIG. 14, relative to a vertical line, the lensframe 706 (and therefore also the lens 1002) is tilted towards the chin area (at an angle of x°). This angle promotes concentration of fresh air flow around the user's nose and mouth, maximizes field of vision towards the patient, and creates room inside the hood at the forehead for optimum aerodynamics and accessories such as an LED light (shown in FIG. 16) and a camera (not shown).

Figure 15:
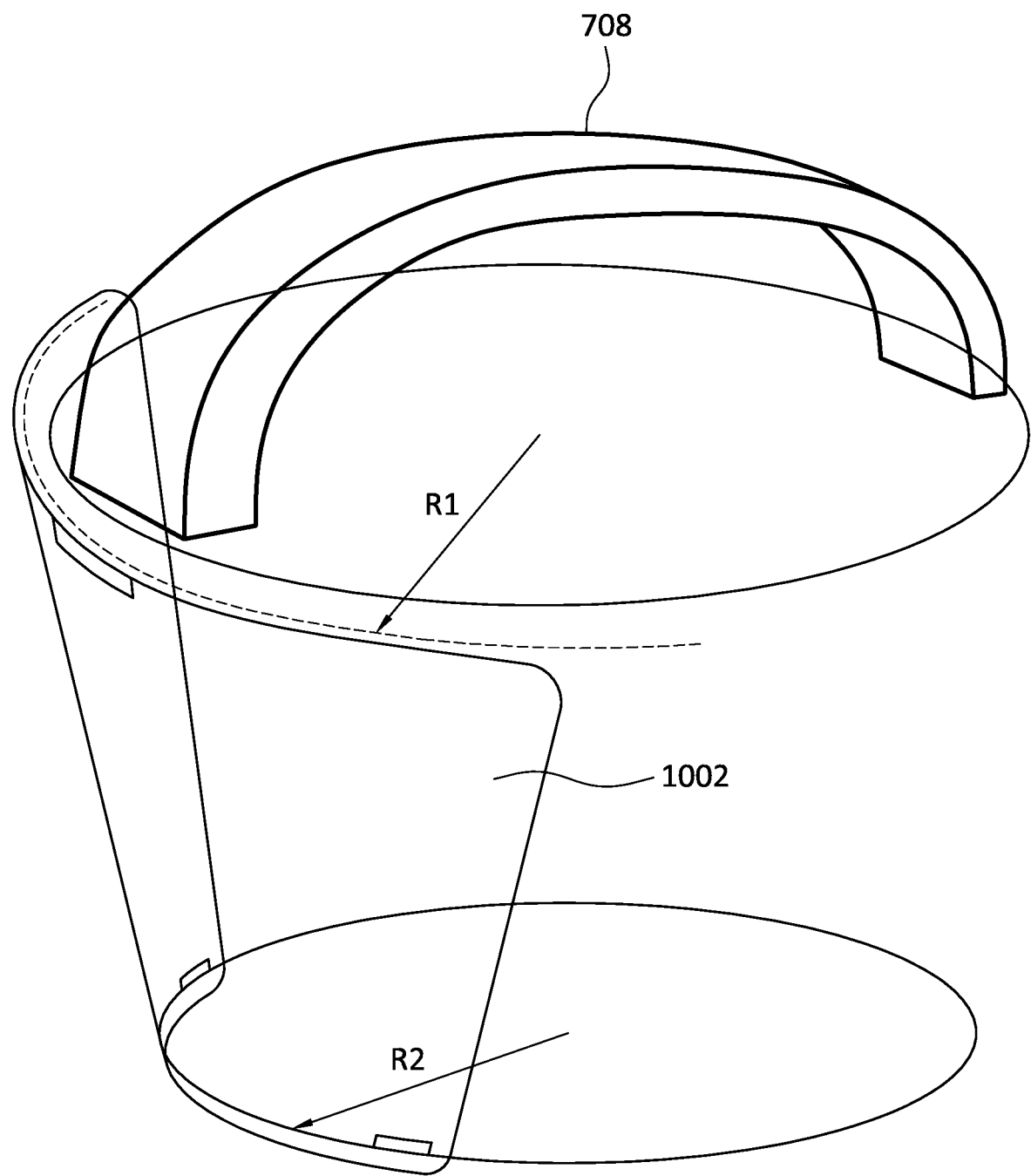

FIG. 15 shows that the lens 1002, as a vision element, is designed as a curve around the user's face area, utilizing an upper radius R1 around the head's vertical centerline and a lower radius R2 around the same centerline. In some embodiments, both radii are the same.

Figure 16:
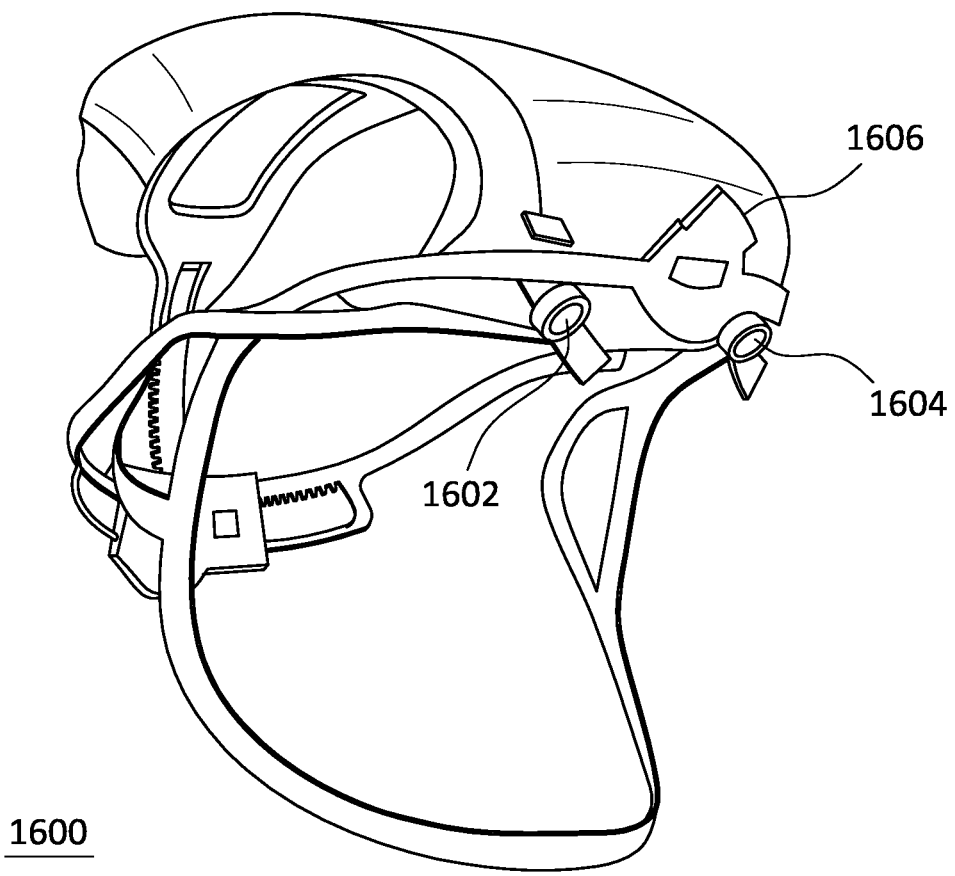
FIG. 16 is a perspective view of an exemplary surgical helmet having two lights in an embodiment of the disclosure.

FIG. 16 shows an embodiment of a surgical helmet 1600 in one embodiment of the disclosure, comprising dual headlamps 1602,1604 and a lens-alignment clip 1606. Conventional surgical helmets typically include only one headlamp. Through user feedback, the inventors discovered that one head-lamp is unsatisfactory, because it provides a narrowly focused beam that is often too dim for surgical purposes. The inventors solved this problem by providing two head-lamps.

Free-Flow Main Air Duct

Figure 17:
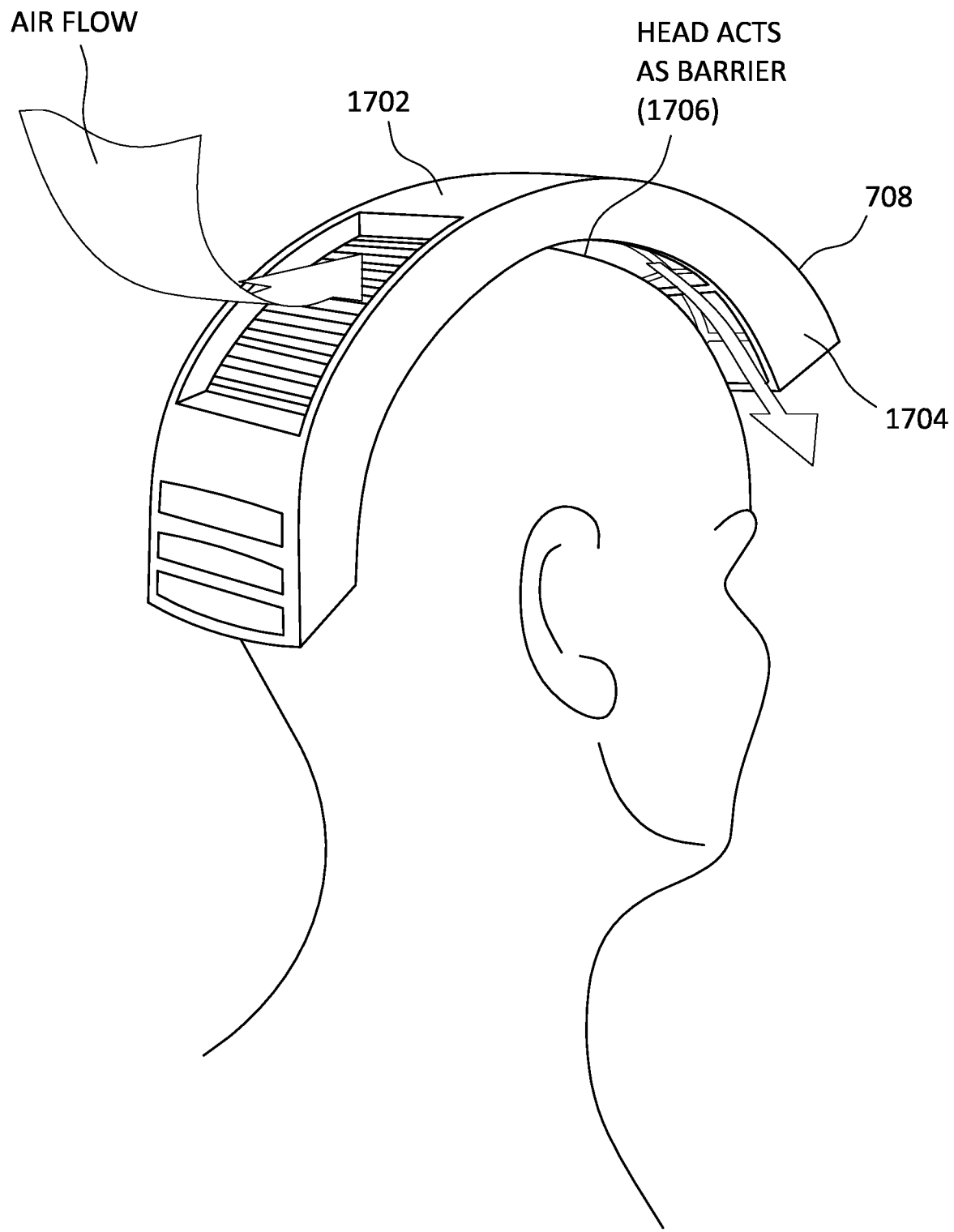
FIGS. 17 and 18 show an exemplary air duct in an exemplary head unit in an embodiment of the disclosure.
Figure 18:
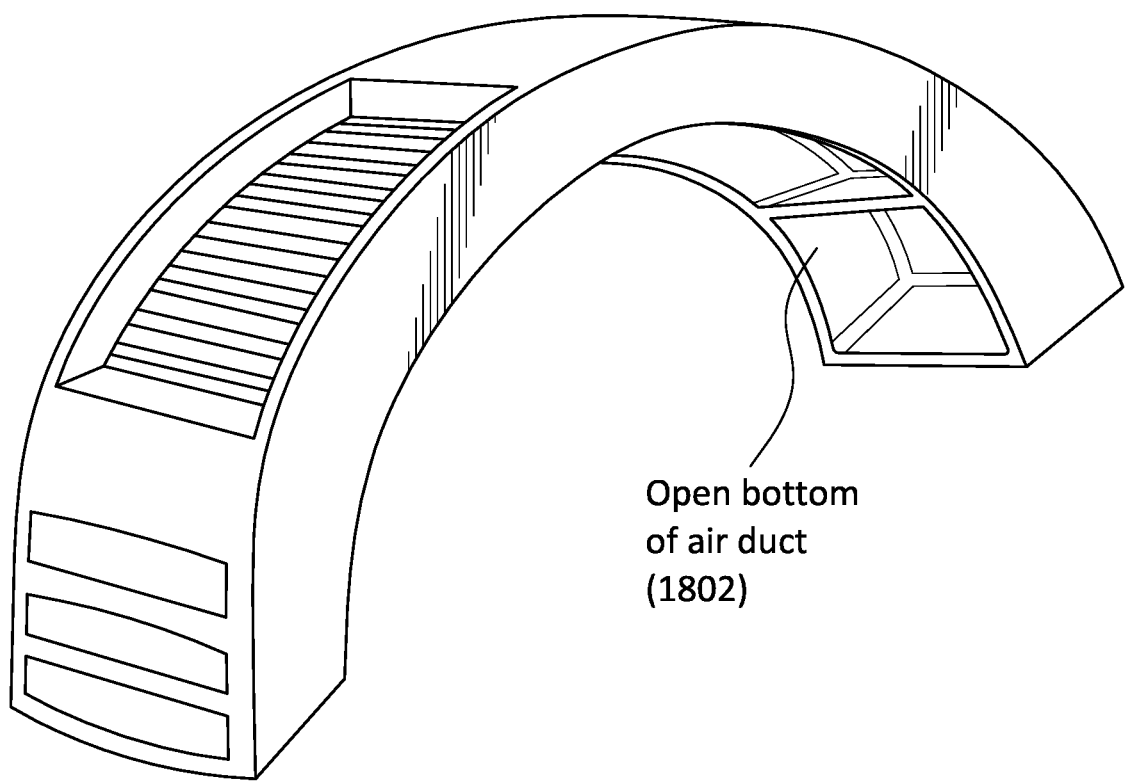

Embodiments of the disclosure may include a free-flow main air duct. FIGS. 17 and 18 show an exemplary free-flow main air duct, in one embodiment of the disclosure.

Because of ergonomic reasons (weight balance), main intake air fans (e.g., fan 208) are commonly located at the back of the head. This requires fresh air to be channeled forward towards a nozzle located in the proximity of the forehead by means of an air duct. Additionally, the upper part of the head (above the hairline) should be flushed with fresh, cool air during use. Furthermore, for a positive ergonomic fit of the system, the helmet assembly should have a relatively low weight and low center of gravity.

As shown in FIGS. 17 and 18, head unit 708 comprises an air duct assembly including one upper surface 1702, two side bounding surfaces (e.g., 1704), and at least one bottom opening (e.g., 1802), arranged such that a fourth bounding surface (or barrier) 1706 is partially formed by the upper part of the skull itself. This configuration allows a reduction of weight, while keeping the head flush above the hairline.

Automatic Airflow Control

Figure 19:
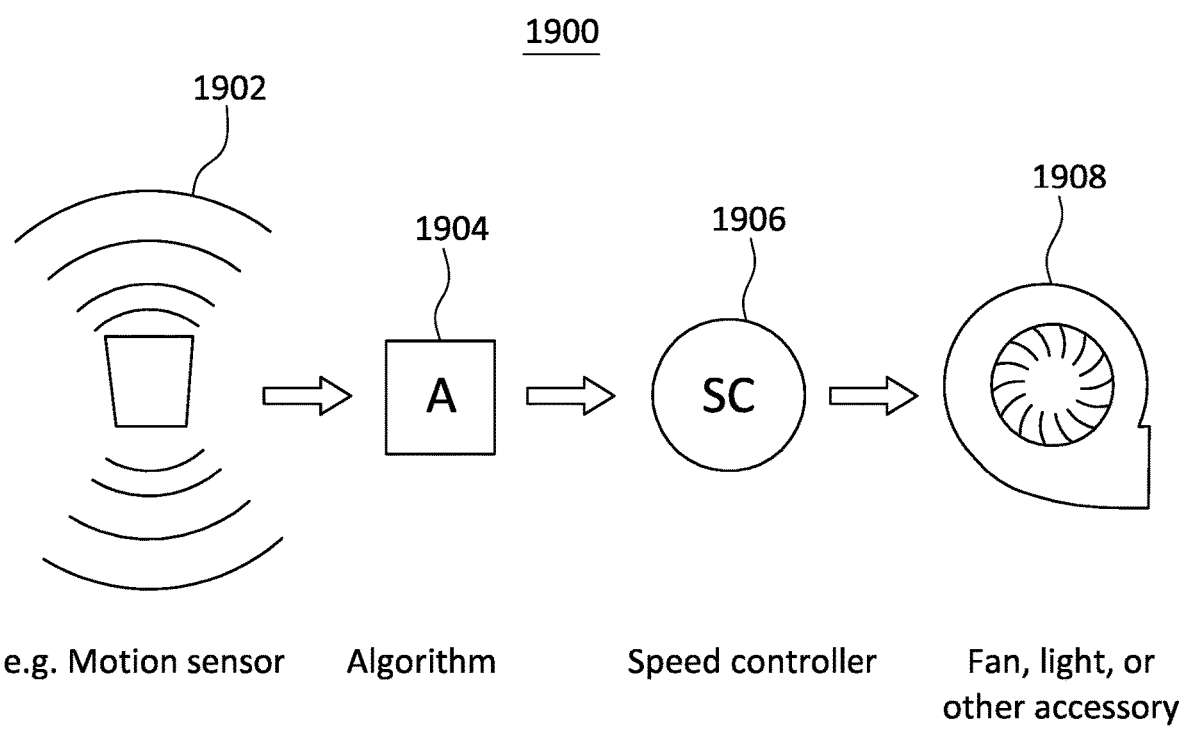
FIG. 19 shows a block diagram of an exemplary touchless control system in an embodiment of the disclosure.

Embodiments of the disclosure may include automatic airflow control. With reference now to FIG. 19, an exemplary automatic airflow control system 1900 in one embodiment of the disclosure is shown.

Automatic airflow control automatically compensates for the microclimatic effects of varying factors, such as physical activity or mental stress levels during surgical procedures, thereby reducing the need for manual adjustment of fan speed during use. This leads to an increased focus on the surgical tasks at hand, as well as a reduced amount of intentional contact between hand and hood/toga, which are by nature potential sources of contamination.

As shown in FIG. 19, one or more sensors 1902 measure direct or indirect microclimatic conditions inside the sterile hood. The sensors 1902 may be located anywhere within hood 704. In one embodiment, the sensors 1902 are positioned on an electronic board (not shown) that is mounted on the head unit 408.

Sensors 1902 are connected to a controller 1904 that is configured to receive one or more sensor signals and generate a fan-speed-control output signal based thereon. In one embodiment, controller 1904 comprises a fan-speed-adjustment (FSA) algorithm that converts the one or more sensor signals into a rate-of-change signal and further translates it (e.g., via an amplifier, a level-shifter, an analog-to-digital converter, a digital-to-analog converter, or an algorithm corresponding to such devices) into an output signal that is sent to the fan-speed control unit 1906. The controller's output signal includes, e.g., the specific information of desired rate of change to the fan speed (RPM) over time and the direction of change (increase or decrease). Finally, variable-speed fan 1908 operates at a speed that is determined by, and corresponds to, the fan-speed control unit's output signal.

In one embodiment, the controller 1904 is a digital processor having software that is configured based on a user's specific personal need or an operating-room or field condition, including, e.g., ambient temperature and ambient sunlight. The digital processor may be a general microprocessor, a digital signal processor, or a digital microcontroller.

Controller 1904 and fan-speed control unit 1906 each may comprise an analog control circuit, a digital processor, a signal processor, or any combination thereof, in accordance with techniques known to those of ordinary skill in the art of control circuitry. Controller 1904 and fan-speed control unit 1906 also may be connected to an audio or visual signaling device (not shown) to indicate the selected fan speed to the user.

Embodiments of the disclosure may include one or more of the following sensor features:

1. Absolute and/or differential temperature measurement, using two temperature sensors, measuring both intake air temperature and the air temperature inside the hood (exhaust air temperature);

2. Humidity sensing, measuring relative humidity of air inside the hood, using a humidity sensor;

3. $CO_2$ sensing, measuring absolute $CO_2$ levels, e.g., by using a non-dispersive infrared detector (NDIR);

4. Motion sensing, measuring static and dynamic acceleration of the head as a representation of physical activity (and therefore heating performance), e.g., via one or more accelerometers;

5. Position or inclination sensing, e.g., via a position sensor or an inclinometer.

6. Voice sensing, e.g., via a microphone;

7. Voice-recognition sensor, e.g., via a microprocessor-based portable computer or smartphone connected to controller 1904 by a wired or wireless interface; and 8. Proximity sensing, e.g., by a capacitive, infrared, or photoelectric sensor.

Figure 20:
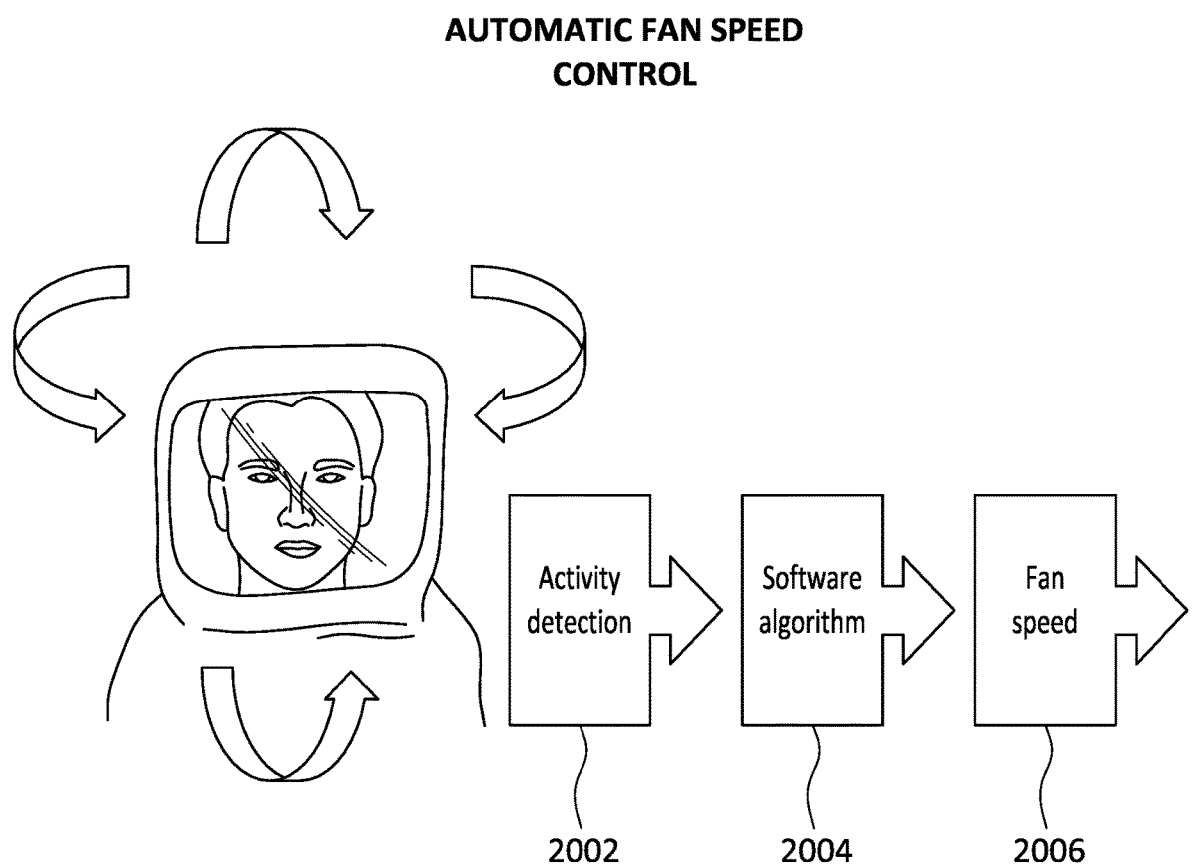
FIGS. 20-22 show exemplary touchless-control sequences and movements.

FIG. 20 shows an embodiment in which the sensors 1902 comprise a motion sensor mounted on head unit 708. In block 2002, the motion sensor detects one or more head movements. In block 2004, the FSA algorithm in controller 1904 determines the quality and quantity of the user's activity based on the detected one or more head movements. In block 2006, the fan-speed control unit automatically adjusts the fan speed based on the determined user activity. For example, during periods of high activity, the controller 1904 produces an output signal that causes the fan-speed control unit 1906 to increase the fan speed. Conversely, during periods of low activity, the controller 1904 produces an output signal that causes the fan-speed control unit 1906 to decrease the fan speed.

At any time during the use of the system, the user can increase or decrease the fan speed manually to adjust the microclimate to his or her actual personal preferences. Such manual adjustment is desirably performed using the touchless user interface, which is described below.

Touchless User Interface

Figure 21:
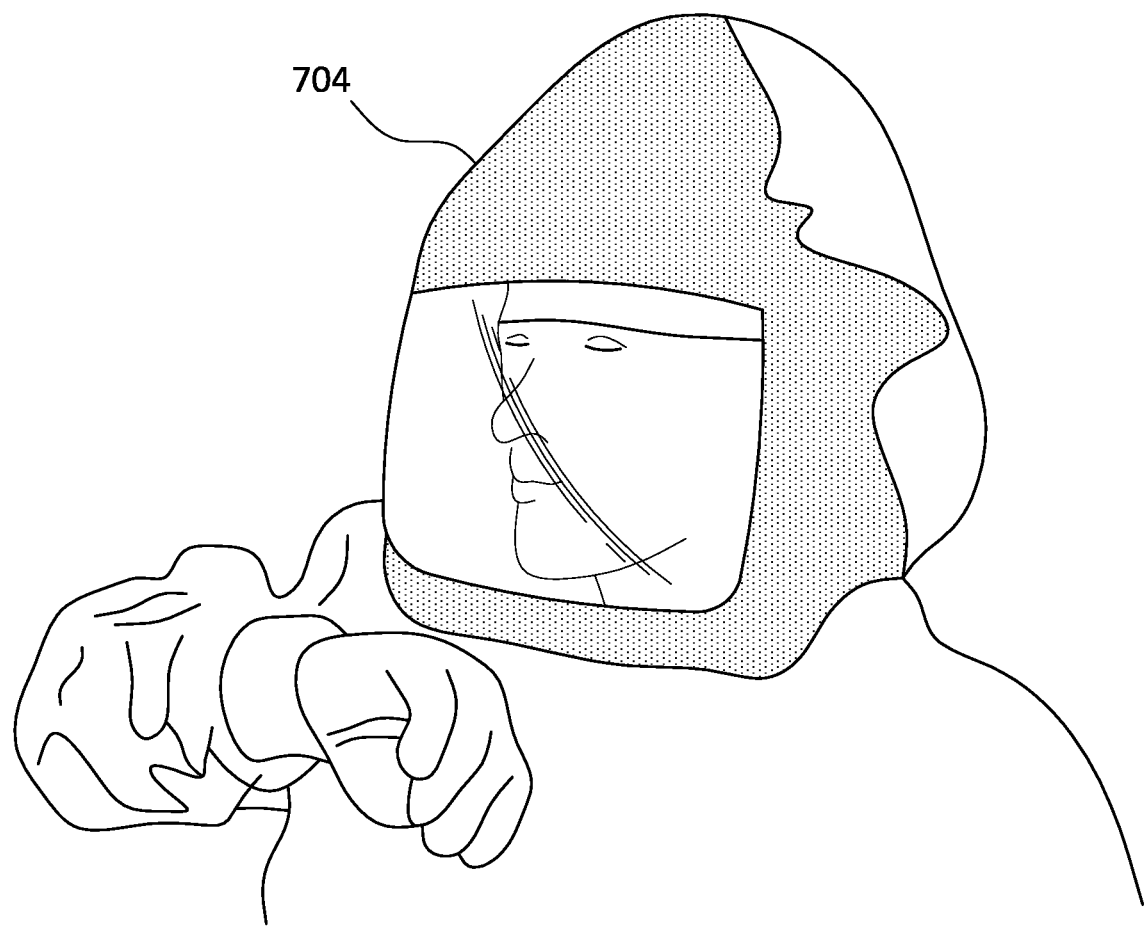

Embodiments of the disclosure may include a touchless user interface. FIG. 21 shows an exemplary method for a user to employ a touchless user interface, in one embodiment of the disclosure. As shown, the user's forearm, wrist, and/or hand approaches his or her chin area up to a distance between 3 cm and 10 cm, and more preferably between 4 cm and 7 cm, and most preferably 5 cm, from the lens frame, always controlling his or her arm position and distance to the sterile hood 702 through visual contact with his or her hand. A proximity sensor (e.g., 1902 in FIG. 19) detects the approach and transmits a control signal to a signal processor (e.g., controller 1904 in FIG. 19). The system acknowledges the signal input with audible and/or visual feedback to the user.

In this embodiment, a capacitive or photoelectric sensor is used as a proximity sensor. State-of-the-art photoelectric sensors are advantageous because of their capability of measuring distance between the sensor and the sensor target. This allows the sensor to discriminate between hand gestures and reduce the risk of unintended inputs by the user.

Furthermore, photoelectric sensors can compensate for transparent materials masking the sensor area. In this embodiment, such compensation is relevant because the sensor is located behind the transparent, sterile lens of the hood 704. Once the sensor input is in line with predefined parameters (e.g., the distance between the user's hand and the sensor), the sensor transmits a signal to a signal-processing unit (e.g., controller 1904). Further processing is described above under the heading "Automatic Airflow Control."

Figure 22:
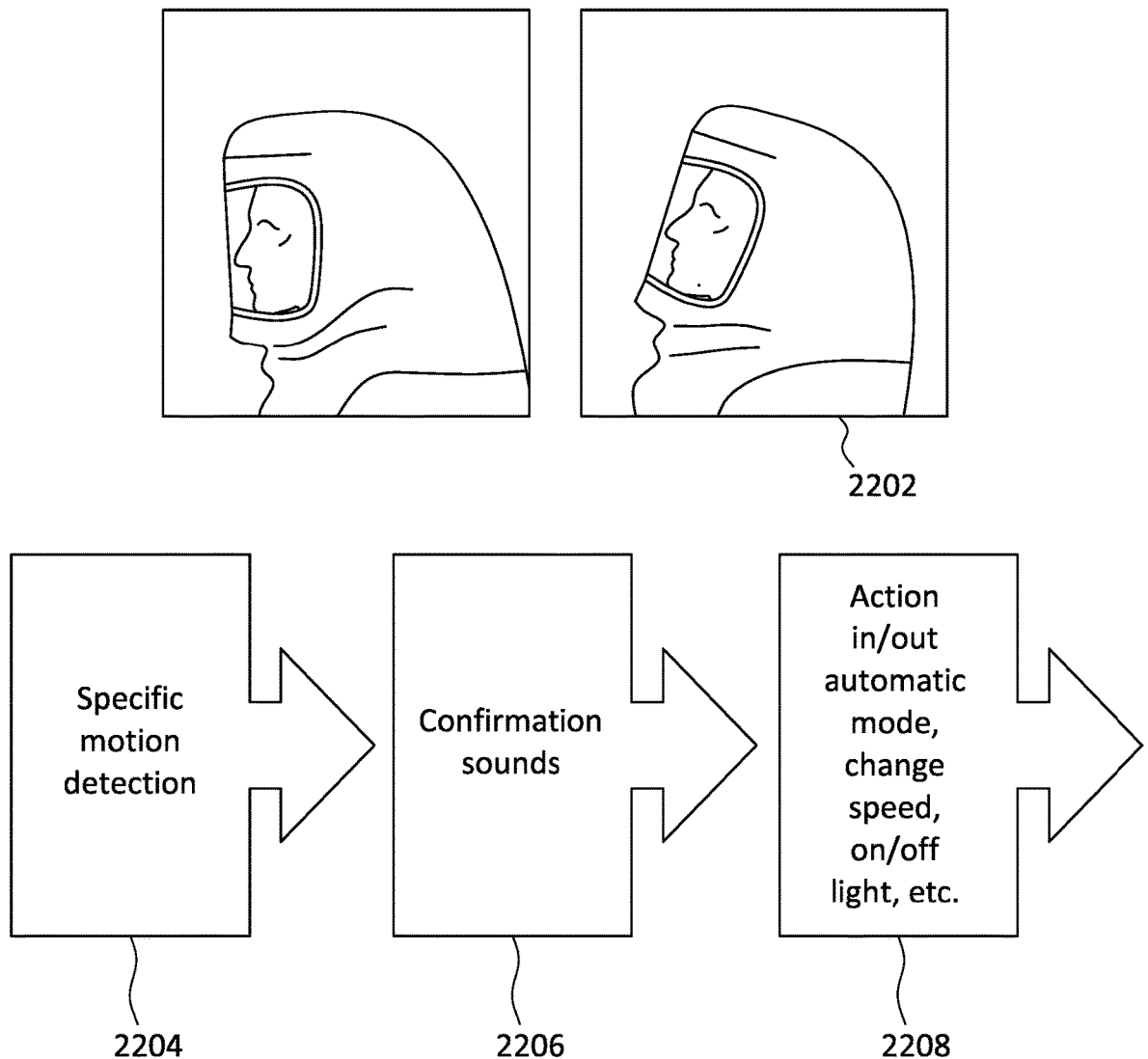

FIG. 22 shows another exemplary method for a user to employ a touchless user interface, in an embodiment of the disclosure. In this embodiment, a motion sensor is mounted on head unit 708. Controller 1904 is configured to monitor the movements of the user's head and to interpret one or more predetermined movements of the user's head (e.g., an unnatural backward head tilt as shown in image 2202) as a specific user input or command. Controller 1904 is further configured to control the fan or other accessories (such as a light or other device) and/or to switch between a manual fan-control mode to an automatic fan-control mode, based on the user's command. In one embodiment, controller 1904 is also configured to respond to a command by generating an audible sound or a visual signal.

Thus, in block 2204, controller 1904 determines that a user's motion corresponds to a predetermined user input. In block 2206, in response to the user input, controller 1904 produces a confirmation sound. And in block 2208, controller 1904 produces a corresponding output signal, e.g., corresponding to an automatic fan-speed mode-control setting, a specific manual fan speed, and/or a light-control setting.

In one embodiment, controller 1904 is configured to provide a user-adjustable, automatic fan-control mode that combines both automatic fan-speed control and manual fan-speed control. The FSA algorithm in controller 1904 automatically selects a fan-speed setpoint that is a function of a temperature gradient, but it also allows the user to adjust the automatically selected setpoint to a higher or lower point, according to the user's needs.

Figure 23:
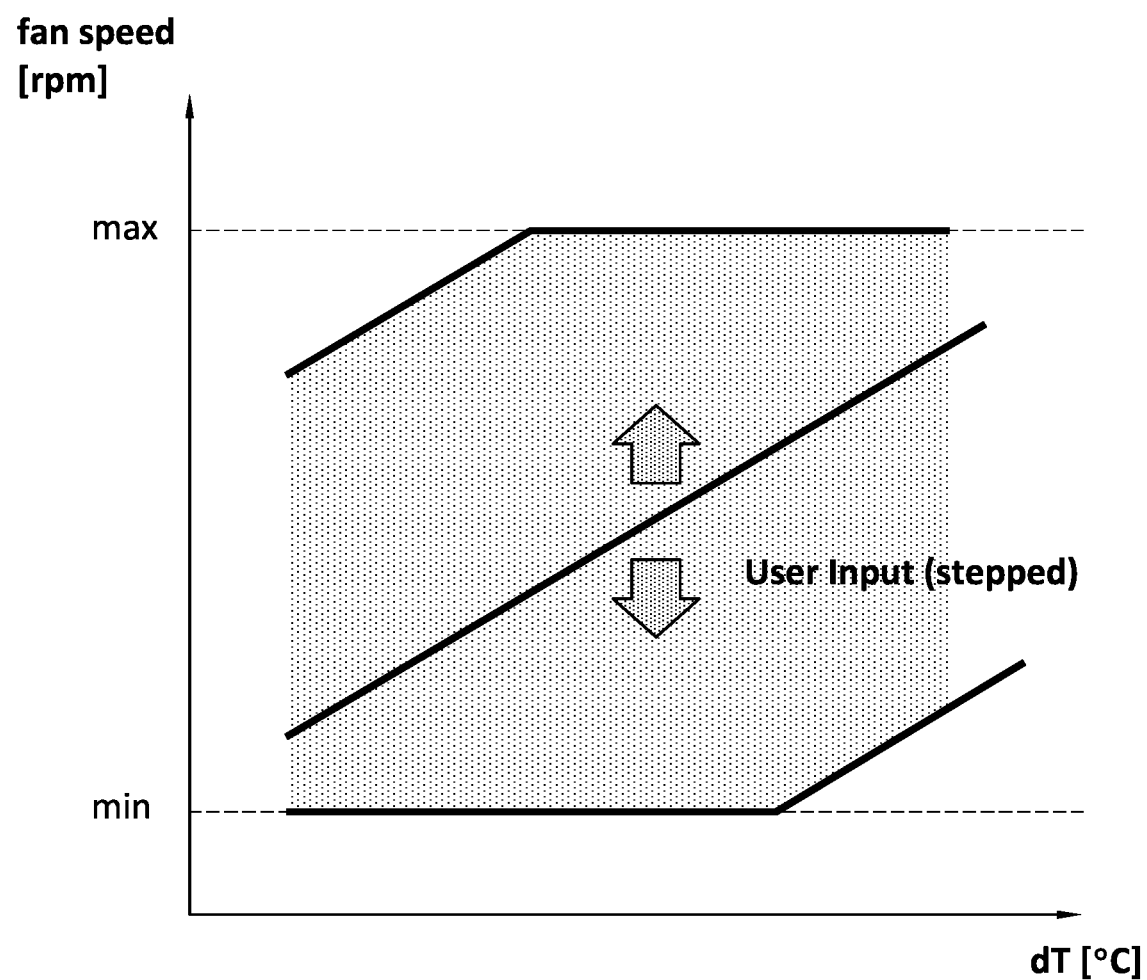
FIG. 23 shows a graph of an exemplary user-adjustable fan speed based on temperature.

FIG. 23 is a plot showing fan speeds automatically selected by the FSA algorithm at different temperature gradients. In one embodiment, the FSA algorithm employs five levels of user adjustability (levels 1 through 5), as shown in the following table:

| | |
|---|---|
| Signal < 2 sec | Shift fan speed algorithm up by equivalent of one level and produce a single audio signal. |
| | If already at level 5, shift FSA down to level 1 and produce a double audio signal. |
| | Each FSA level has his specific audio signal frequency |
| Signal > 2 sec | Switch Light on/off |
| Without Signal | FSA does adjust fan speed dynamically, based on dT, dRH, dCO2 level or head motion input |
| | Autonomous FSA adjustment without audio signal and not recognizable by user due to stepless adjustment |
| Repower the system after disruption (battery disconnection) | Shift fan speed algorithm to equivalent of fan Level 3 |

Reference herein to "one embodiment" or "an embodiment" means that a particular feature, structure, or characteristic described in connection with the embodiment can be included in at least one embodiment of the disclosure. The appearances of the phrase "in one embodiment" in various places in the specification are not necessarily all referring to the same embodiment, nor are separate or alternative embodiments necessarily mutually exclusive of other embodiments.

Although the disclosure has been set forth in terms of the exemplary embodiments described herein and illustrated in the attached drawings, it is to be understood that such disclosure is purely illustrative and is not to be interpreted as limiting. Consequently, various alterations, modifications, and/or alternative embodiments and applications may be suggested to those skilled in the art after having read this disclosure. Accordingly, it is intended that the disclosure be interpreted as encompassing all alterations, modifications, or alternative embodiments and applications as fall within the true spirit and scope of this disclosure.

The invention claimed is:

1. A barrier system, said system comprising:
    a head unit shaped to be worn over a head of a wearer;
    a hood positioned over the head unit and forming a chamber;
    one or more sensors located within the chamber and configured to produce one or more sensor-output signals; and
    a controller connected to the one or more sensors and configured to produce one or more controller-output signals based on the one or more sensor-output signals;
    wherein the head unit comprises an electric fan and a fan housing, wherein the fan housing has a top end portion, a bottom end portion and a mounting plate positioned between the top end portion and the bottom end portion, the top end portion being configured with a single intake air duct formed by a wall extending away from the top end portion of the head unit thereby defining a planar perimeter sealing edge and a concave recess within the planar perimeter sealing edge, wherein the concave recess comprises a diameter at the top end portion that is larger than a diameter at the bottom end portion; and wherein the electric fan and the mounting plate are disposed within the concave recess at a position below the planar perimeter sealing edge, and wherein the electric fan is mounted on a bottom surface of the mounting plate, a top surface of the mounting plate forms part of the single intake duct, and the bottom surface of the mounting plate and a bottom most interior surface of the fan housing form a fan outlet duct, and wherein the planar perimeter sealing edge forms a top most surface of the fan housing, wherein the entire planar perimeter sealing edge is a free end forming a single inlet opening.

2. The barrier system of claim 1, wherein the one or more sensors are configured to detect one or more of: ambient temperature, chamber temperature, intake-air temperature, exhaust-air temperature, humidity, CO2 level, motion, position, inclination, voice sounds, voice-recognized words, and an object's proximity.

3. The barrier system of claim 1, wherein:
the one or more sensors comprise one or more motion sensors mounted on the head unit; and
the controller is configured to produce the one or more controller-output signals based on a predetermined head movement.

4. The barrier system of claim 1, wherein:
the one or more sensors comprise a proximity sensor positioned near the head unit; and
the controller is configured to produce the one or more controller-output signals based on a predetermined distance of the proximity sensor to an object.

5. The barrier system of claim 1, further comprising a signaling device connected to the controller, wherein the controller is configured to activate the signaling device.

6. The barrier system of claim 1, further comprising:
a fan-speed control unit connected to the controller;
wherein the electric fan connected to the fan-speed control unit; and
wherein the fan-speed control unit is configured to select a fan speed based on the one or more controller-output signals.

7. The barrier system of claim 6, wherein the controller comprises a fan speed-adjustment algorithm that converts the one or more sensor signals into a rate of change signal.

8. The barrier system of claim 6, wherein:
the controller comprises either (a) at least one of the following circuits: (1) an amplifier, (2) a level-shifter, (3) an analog-to-digital converter, and (4) a digital-to-analog
converter, or (b) an algorithm corresponding to one or more of such the at least one of the circuits,
and
the controller is configured to translate the one or more sensor-output signals into one or more controller-output signals either by connecting the one or more
sensor-output signals to at least one of the circuits identified in (a)(1) through (a)(4) above, or by executing an algorithm corresponding to such the at least one of the circuits.

9. The barrier system of claim 6, wherein the one or more controller-output signals includes at least one of (a) information about a desired rate of change to the fan speed over time and (b) a direction of a desired change.

10. The barrier system of claim 1, wherein the electric fan is coupled to the fan outlet duct, the fan outlet duct directing air in a path orthogonal to the direction of the intake air.

11. A method of controlling an electric fan inside a barrier system comprising
a head unit, a hood, one or more sensors, and a controller, the method comprising:
(a) sensing one or more characteristics;
(b) producing one or more sensor signals based on the sensed one or more characteristics;
(c) converting or processing the one or more sensor signals to produce one or more controller-output signals; and
(d) controlling a speed of the electric fan based on the one or more controller-output signals;
wherein the head unit comprises the electric fan and a fan housing, wherein the fan housing has a top end portion, a bottom end portion and a mounting plate positioned between the top end portion and the bottom end portion, the top end portion being configured with a single intake air duct formed by a wall extending away from the top end portion of the head unit thereby defining a planar perimeter sealing edge and a concave recess within the planar perimeter sealing edge, wherein the concave recess comprises a diameter at the top end portion that is larger than a diameter at the bottom end portion; and wherein the electric fan and the mounting plate are disposed within the concave recess at a position below the planar perimeter sealing edge, and wherein the electric fan is mounted on a bottom surface of the mounting plate, a top surface of the mounting plate forms part of the single intake duct, and the bottom surface of the mounting plate and a bottom most interior surface of the fan housing form a fan outlet duct, and wherein the planar perimeter sealing edge forms a top most surface of the fan housing, wherein the entire planar perimeter sealing edge is a free end forming a single inlet opening.

12. The method of claim 11, wherein the one or more characteristics comprise one or more of: ambient temperature, chamber temperature, intake-air temperature, exhaust-air temperature, humidity, CO2 level, motion, position, inclination, voice sounds, voice-recognized words, and an object's proximity.

13. The method of claim 11, wherein the characteristic is the head unit's movement, and step (b) comprises producing the one or more sensor signals based on a predetermined head movement.

14. The method of claim 11, wherein the characteristic is an object's proximity to the head unit, and step (b) comprises producing the one or more sensor signals based on a predetermined proximity.

15. The method of claim 11, further comprising activating a signaling device.

16. The method of claim 11, wherein converting or processing the one or more sensor signals to produce one or more controller-output signals comprises converting one or more sensor signals to one or more rate-of-change signals.

17. The method of claim 11, wherein converting or processing the one or more sensor signals to produce one or more controller-output signals comprises at least one of the following:
(a) amplifying the one or more sensor signals,
(b) level-shifting the one or more sensor signals,
(c) converting the one or more sensor signals from analog signals to digital signals,
(d) converting the one or more sensor signals from digital signals to analog signals, and
(e) executing an algorithm that is configured to produce an output corresponding to one or more of steps (a) through (d).

18. The method of claim 11, wherein converting or processing the one or more sensor signals to produce one or more controller-output signals comprises at least one of:
 (a) determining a desired rate of change to the fan speed over time, and (b) determining a direction of a desired change.

19. The method of claim 11, wherein the electric fan is coupled to fan outlet duct, the fan outlet duct directing air in a path orthogonal to the direction of the intake air.

* * * * *